United States Patent
Torrance et al.

(10) Patent No.: US 11,478,349 B2
(45) Date of Patent: Oct. 25, 2022

(54) SYSTEMS, DEVICES, AND METHODS FOR COUPLING A PROSTHETIC IMPLANT TO A FENESTRATED BODY

(71) Applicant: Bolton Medical, Inc., Sunrise, FL (US)

(72) Inventors: Casey Torrance, Snohomish, WA (US); Shannon Eubanks, Woodinville, WA (US)

(73) Assignee: Bolton Medical, Inc., Sunrise, FL (US)

( * ) Notice: Subject to any disclaimer, the term of this patent is extended or adjusted under 35 U.S.C. 154(b) by 42 days.

(21) Appl. No.: 16/825,043

(22) Filed: Mar. 20, 2020

(65) Prior Publication Data

US 2020/0352700 A1    Nov. 12, 2020

Related U.S. Application Data

(63) Continuation of application No. PCT/US2018/052400, filed on Sep. 24, 2018.
(Continued)

(51) Int. Cl.
*A61F 2/07* (2013.01)
*A61F 2/954* (2013.01)
(Continued)

(52) U.S. Cl.
CPC ............... *A61F 2/07* (2013.01); *A61F 2/954* (2013.01); *A61F 2/958* (2013.01);
(Continued)

(58) Field of Classification Search
CPC ...... A61F 2/07–2002/077; A61F 2/954; A61F 2/958; A61F 2250/0069; A61F 2210/0057
See application file for complete search history.

(56) References Cited

U.S. PATENT DOCUMENTS 4,787,391 A    11/1988   Elefteriades
5,123,917 A    6/1992   Lee
(Continued)

FOREIGN PATENT DOCUMENTS

CN    104240220 A    12/2014
CN    107157616 A    9/2017
(Continued)

OTHER PUBLICATIONS

Chuter et al., "Fenestrated and Branched Stent-Grafts for thoracoabdominal, Pararenal and Juxtarenal Aortic Aneurysm Repair," Seminars in Vascular Surgery, 20:90-96 (2007).
(Continued)

*Primary Examiner* — Rebecca S Preston
(74) *Attorney, Agent, or Firm* — Foley Hoag LLP

(57) ABSTRACT

Devices, systems, and methods for implanting a patient-specific prosthesis at a treatment site in a patient are disclosed herein. In some embodiments, a patient-specific prosthesis includes a tubular graft and a coupling member. A fenestration can be disposed in the tubular graft, the fenestration corresponding to a predicted branch blood vessel location. The coupling member can be disposed about the fenestration. The coupling member can include a coil configured to expand from a first configuration to a second configuration in response to the application of an expanding force. The coil can be configured to contract to a third configuration upon removal of the expanding force.

13 Claims, 14 Drawing Sheets

Related U.S. Application Data

(60) Provisional application No. 62/562,776, filed on Sep. 25, 2017.

(51) Int. Cl.
*A61F 2/958* (2013.01)
*A61F 2/06* (2013.01)

(52) U.S. Cl.
CPC . *A61F 2002/061* (2013.01); *A61F 2002/9583* (2013.01); *A61F 2210/0014* (2013.01); *A61F 2210/0057* (2013.01); *A61F 2220/0025* (2013.01); *A61F 2250/001* (2013.01); *A61F 2250/0039* (2013.01); *A61F 2250/0069* (2013.01); *A61F 2250/0098* (2013.01)

(56) References Cited

U.S. PATENT DOCUMENTS

| | | |
|---|---|---|
| 5,370,692 A | 12/1994 | Fink et al. |
| 5,507,769 A | 4/1996 | Marin et al. |
| 5,607,444 A | 3/1997 | Lam |
| 5,755,769 A | 5/1998 | Richard et al. |
| 5,984,955 A | 11/1999 | Wisselink |
| 6,030,414 A | 2/2000 | Taheri |
| 6,036,702 A | 3/2000 | Bachinski et al. |
| 6,059,824 A | 5/2000 | Taheri |
| 6,171,334 B1 | 1/2001 | Cox |
| 6,280,464 B1 | 8/2001 | Hayashi |
| 6,395,018 B1 | 5/2002 | Castaneda |
| 6,524,335 B1 | 2/2003 | Hartley et al. |
| 6,616,675 B1 | 9/2003 | Evard et al. |
| 6,719,768 B1 | 4/2004 | Cole et al. |
| 7,112,216 B2 | 9/2006 | Gregorich |
| 7,197,170 B2 | 3/2007 | Dwyer et al. |
| 7,306,623 B2 | 12/2007 | Watson |
| 7,413,573 B2 | 8/2008 | Hartley et al. |
| 7,435,253 B1 | 10/2008 | Hartley et al. |
| 7,575,590 B2 | 8/2009 | Watson |
| 7,678,141 B2 | 3/2010 | Greenan et al. |
| 7,722,664 B2 | 5/2010 | Zarbatany et al. |
| 7,763,063 B2 | 7/2010 | Arbefeuille et al. |
| 7,833,266 B2 | 11/2010 | Gregorich et al. |
| 7,937,660 B2 | 5/2011 | Binkert |
| 8,007,605 B2 | 8/2011 | Arbefeuille et al. |
| 8,048,140 B2 | 11/2011 | Purdy |
| 8,062,345 B2 | 11/2011 | Ouellette et al. |
| 8,062,349 B2 | 11/2011 | Moore et al. |
| 8,070,790 B2 | 12/2011 | Berra et al. |
| 8,172,895 B2 | 5/2012 | Anderson et al. |
| 8,216,298 B2 | 7/2012 | Wright et al. |
| 8,236,040 B2 | 8/2012 | Mayberry et al. |
| 8,249,815 B2 | 8/2012 | Taylor |
| 8,287,586 B2 | 10/2012 | Schaeffer et al. |
| 8,292,943 B2 | 10/2012 | Berra et al. |
| 8,308,790 B2 | 11/2012 | Arbefeuille et al. |
| 8,337,547 B2 | 12/2012 | Iancea et al. |
| 8,359,118 B2 | 1/2013 | Ono et al. |
| 8,449,595 B2 | 5/2013 | Ouellette et al. |
| 8,480,725 B2 | 7/2013 | Rasmussen et al. |
| 8,500,792 B2 | 8/2013 | Berra |
| 8,636,788 B2 | 1/2014 | Arbefeuille et al. |
| 8,641,752 B1 | 2/2014 | Holm et al. |
| 8,682,626 B2 | 3/2014 | Ionasec et al. |
| 8,682,686 B2 | 3/2014 | Warner et al. |
| 8,740,963 B2 | 6/2014 | Arbefeuille et al. |
| 8,808,351 B2 | 8/2014 | Osborne |
| 8,831,302 B2 | 9/2014 | Mahfouz |
| 8,897,513 B2 | 11/2014 | Balasubramanian |
| 8,945,202 B2 | 2/2015 | Mayberry et al. |
| 8,958,623 B1 | 2/2015 | Grady et al. |
| 8,989,460 B2 | 3/2015 | Mahfouz |
| 9,095,421 B2 | 8/2015 | Peterson |
| 9,101,455 B2 | 8/2015 | Roeder et al. |
| 9,125,733 B2 | 9/2015 | Greenberg et al. |
| 9,149,381 B2 | 10/2015 | Schreck et al. |
| 9,173,755 B2 | 11/2015 | Berra et al. |
| 9,198,786 B2 | 12/2015 | Moore et al. |
| 9,220,617 B2 | 12/2015 | Berra |
| 9,259,336 B2 | 2/2016 | Schaeffer et al. |
| 9,305,123 B2 | 4/2016 | Leotta et al. |
| 9,320,631 B2 | 4/2016 | Moore et al. |
| 9,333,104 B2 | 5/2016 | Ouellette et al. |
| 9,364,314 B2 | 6/2016 | Berra et al. |
| 9,408,734 B2 | 8/2016 | Arbefeuille et al. |
| 9,408,735 B2 | 8/2016 | Arbefeuille et al. |
| 9,439,751 B2 | 9/2016 | White et al. |
| 9,561,124 B2 | 2/2017 | Arbefeuille et al. |
| 9,566,149 B2 | 2/2017 | Shaw |
| 9,603,696 B2 | 3/2017 | Hartley et al. |
| 9,629,686 B2 | 4/2017 | Van Bibber et al. |
| 9,629,705 B2 | 4/2017 | Douthitt et al. |
| 9,649,211 B2 | 5/2017 | Bonsignore et al. |
| 9,655,712 B2 | 5/2017 | Berra et al. |
| 9,694,108 B2 | 7/2017 | Cully et al. |
| 9,724,187 B2 | 8/2017 | Ivancev et al. |
| 9,737,394 B2 | 8/2017 | Coghlan et al. |
| 9,801,741 B1 | 10/2017 | Thapliyal |
| 9,811,613 B2 | 11/2017 | Leotta et al. |
| 9,861,503 B2 | 1/2018 | Barthold et al. |
| 9,877,857 B2 | 1/2018 | Arbefeuille et al. |
| 9,907,686 B2 | 3/2018 | Ouellette et al. |
| 9,913,743 B2 | 3/2018 | Arbefeuille et al. |
| 9,925,080 B2 | 3/2018 | Arbefeuille et al. |
| 10,004,616 B2 | 6/2018 | Chakfe et al. |
| 10,105,248 B2 | 10/2018 | Berra et al. |
| 10,105,250 B2 | 10/2018 | Berra |
| 10,245,137 B2 | 4/2019 | Scutti et al. |
| 10,390,931 B2 | 8/2019 | Douthitt et al. |
| 10,390,932 B2 | 8/2019 | Lostetter |
| 10,485,684 B2 | 11/2019 | Marmur et al. |
| 10,512,556 B2 | 12/2019 | Longo et al. |
| 10,653,484 B2 | 5/2020 | Van Bibber et al. |
| 10,702,406 B2 | 7/2020 | Swift et al. |
| 11,000,359 B2 | 5/2021 | Torrance et al. |
| 2002/0042564 A1 | 4/2002 | Cooper et al. |
| 2002/0042622 A1 | 4/2002 | Vargas et al. |
| 2002/0062133 A1 | 5/2002 | Gilson et al. |
| 2002/0095205 A1 | 7/2002 | Edwin et al. |
| 2002/0188344 A1 | 12/2002 | Bolea et al. |
| 2002/0193872 A1 | 12/2002 | Trout et al. |
| 2003/0093145 A1 | 5/2003 | Lawrence-Brown et al. |
| 2004/0034406 A1 | 2/2004 | Thramann |
| 2004/0064081 A1 | 4/2004 | Stanish |
| 2004/0102866 A1 | 5/2004 | Harris et al. |
| 2004/0138737 A1 | 7/2004 | Davidson et al. |
| 2005/0049667 A1 | 3/2005 | Arbefeuille et al. |
| 2005/0102021 A1* | 5/2005 | Osborne .................. A61F 2/07 623/1.13 |
| 2005/0131517 A1 | 6/2005 | Hartley et al. |
| 2005/0131523 A1 | 6/2005 | Bashiri et al. |
| 2005/0137518 A1 | 6/2005 | Biggs et al. |
| 2006/0020319 A1 | 1/2006 | Kim et al. |
| 2006/0058638 A1 | 3/2006 | Boese et al. |
| 2006/0116749 A1 | 6/2006 | Willink et al. |
| 2006/0135985 A1 | 6/2006 | Cox et al. |
| 2006/0259116 A1 | 11/2006 | Feld et al. |
| 2007/0055358 A1 | 3/2007 | Krolik et al. |
| 2007/0055360 A1 | 3/2007 | Hanson et al. |
| 2007/0106368 A1 | 5/2007 | Vonderwalde |
| 2007/0142900 A1 | 6/2007 | Balaji |
| 2007/0244547 A1 | 10/2007 | Greenan |
| 2007/0293936 A1 | 12/2007 | Dobak |
| 2008/0091260 A1 | 4/2008 | Pomeranz et al. |
| 2008/0109066 A1 | 5/2008 | Quinn |
| 2008/0147174 A1 | 6/2008 | Konstantino et al. |
| 2008/0201007 A1 | 8/2008 | Boyden et al. |
| 2008/0255582 A1 | 10/2008 | Harris |
| 2008/0264102 A1 | 10/2008 | Berra |
| 2008/0269867 A1 | 10/2008 | Johnson |
| 2009/0030502 A1 | 1/2009 | Sun et al. |
| 2009/0163994 A1 | 6/2009 | Quigley et al. |
| 2009/0204228 A1 | 8/2009 | Hiles |
| 2009/0264990 A1 | 10/2009 | Bruszewski et al. |

(56) References Cited

U.S. PATENT DOCUMENTS

| | | |
|---|---|---|
| 2009/0304245 A1 | 12/2009 | Egger et al. |
| 2010/0004730 A1 | 1/2010 | Benjamin et al. |
| 2010/0063576 A1 | 3/2010 | Schaeffer et al. |
| 2010/0121429 A1 | 5/2010 | Greenan et al. |
| 2010/0268319 A1 | 10/2010 | Bruszewski et al. |
| 2011/0257720 A1 | 10/2011 | Peterson et al. |
| 2011/0270378 A1 | 11/2011 | Bruszewski et al. |
| 2012/0035714 A1 | 2/2012 | Ducke et al. |
| 2012/0046728 A1 | 2/2012 | Huser et al. |
| 2013/0116775 A1 | 5/2013 | Roeder et al. |
| 2013/0123900 A1 | 5/2013 | Eblacas et al. |
| 2013/0158648 A1 | 6/2013 | Hartley et al. |
| 2013/0296998 A1 | 11/2013 | Leotta et al. |
| 2013/0338760 A1 | 12/2013 | Aristizabal et al. |
| 2014/0046428 A1 | 2/2014 | Cragg et al. |
| 2014/0172072 A1 | 6/2014 | Shalev |
| 2014/0180393 A1 | 6/2014 | Roeder |
| 2014/0277335 A1 | 9/2014 | Greenberg et al. |
| 2014/0277340 A1 | 9/2014 | White et al. |
| 2014/0350658 A1 | 11/2014 | Benary et al. |
| 2015/0005868 A1 | 1/2015 | Koskas et al. |
| 2015/0105849 A1 | 4/2015 | Cohen et al. |
| 2015/0202067 A1 | 7/2015 | Barrand et al. |
| 2015/0209163 A1 | 7/2015 | Kelly |
| 2015/0234957 A1 | 8/2015 | Leotta et al. |
| 2015/0238121 A1 | 8/2015 | Tu et al. |
| 2015/0313596 A1 | 11/2015 | Todd |
| 2015/0332455 A1 | 11/2015 | Kobayashi et al. |
| 2016/0022450 A1 | 1/2016 | Hehrlein |
| 2016/0184078 A1 | 6/2016 | Choubey et al. |
| 2017/0049588 A1 | 2/2017 | Davis et al. |
| 2017/0281382 A1 | 10/2017 | Lostetter et al. |
| 2017/0333133 A1 | 11/2017 | Van Bibber et al. |
| 2017/0333175 A1 | 11/2017 | Douthitt et al. |
| 2018/0021130 A1 | 1/2018 | Danino |
| 2018/0064529 A1 | 3/2018 | Sibe |
| 2018/0116832 A1 | 5/2018 | Pillai |
| 2018/0153680 A1 | 6/2018 | Greenberg et al. |
| 2018/0228593 A1 | 8/2018 | Eaton et al. |
| 2018/0235787 A1 | 8/2018 | Bolduc et al. |
| 2018/0303641 A1 | 10/2018 | Roeder et al. |
| 2019/0021839 A1 | 1/2019 | Kolbel |
| 2019/0050507 A1 | 2/2019 | Leotta et al. |
| 2019/0083229 A1 | 3/2019 | Szente Varga |
| 2019/0231514 A1 | 8/2019 | Arbefeuille |
| 2019/0231568 A1 | 8/2019 | Garcia |
| 2019/0231571 A1 | 8/2019 | Lostetter |
| 2019/0247178 A1 | 8/2019 | Arbefeuille |
| 2019/0247179 A1 | 8/2019 | Lostetter |
| 2019/0247213 A1 | 8/2019 | Lostetter |
| 2019/0269497 A1 | 9/2019 | Arbefeuille |
| 2019/0269498 A1 | 9/2019 | Arbefeuille et al. |
| 2019/0269537 A1 | 9/2019 | Arbefeuille |
| 2019/0282355 A1 | 9/2019 | Lostetter |
| 2019/0321207 A1 | 10/2019 | Arbefeuille et al. |
| 2019/0328556 A1 | 10/2019 | Eubanks et al. |
| 2019/0388213 A1 | 12/2019 | Torrance et al. |
| 2020/0146808 A1 | 5/2020 | Kratzberg et al. |
| 2020/0246165 A1 | 8/2020 | Arbefeuille et al. |
| 2020/0289256 A1 | 9/2020 | Szente Varga |
| 2020/0352700 A1 | 11/2020 | Torrance et al. |

FOREIGN PATENT DOCUMENTS

| | | |
|---|---|---|
| EP | 0786972 B1 | 1/2004 |
| EP | 2471498 A1 | 7/2012 |
| EP | 2517672 A1 | 10/2012 |
| EP | 2 606 851 A1 | 6/2013 |
| EP | 2735283 A1 | 5/2014 |
| EP | 2740440 A2 | 6/2014 |
| EP | 2745812 A1 | 6/2014 |
| EP | 2745813 A1 | 6/2014 |
| EP | 2749250 A1 | 7/2014 |
| EP | 2749251 A1 | 7/2014 |
| EP | 3040054 A1 | 7/2016 |
| EP | 3078349 A1 | 10/2016 |
| EP | 3146993 A1 | 3/2017 |
| EP | 3272319 A1 | 1/2018 |
| FR | 2932979 A1 | 1/2010 |
| JP | 2012/152549 A | 8/2012 |
| WO | WO-97/03624 A1 | 2/1997 |
| WO | WO-97/48350 A1 | 12/1997 |
| WO | WO-01/60285 A1 | 8/2001 |
| WO | WO-02/29758 A2 | 4/2002 |
| WO | WO-02/083038 A2 | 10/2002 |
| WO | WO-03/099108 A2 | 12/2003 |
| WO | WO-2005/034809 A1 | 4/2005 |
| WO | WO-2006/037086 A1 | 4/2006 |
| WO | WO-2007045000 A2 | 4/2007 |
| WO | WO-2008/124222 A1 | 10/2008 |
| WO | WO-2009/148594 A1 | 12/2009 |
| WO | WO-2010/024867 A1 | 3/2010 |
| WO | WO-2010/024880 A1 | 3/2010 |
| WO | WO-2010/030370 A1 | 3/2010 |
| WO | WO-2010/127040 A1 | 11/2010 |
| WO | WO-2012/116368 A2 | 8/2012 |
| WO | WO-2012/145823 A1 | 11/2012 |
| WO | WO-2014/53616 A1 | 4/2014 |
| WO | WO-2014/149022 A1 | 9/2014 |
| WO | WO-2015/059019 A1 | 4/2015 |
| WO | WO-2015/070792 A1 | 5/2015 |
| WO | WO-2017/007947 A1 | 1/2017 |
| WO | WO-2017/218474 A1 | 12/2017 |
| WO | WO-2019/060816 A2 | 3/2019 |
| WO | WO-2020/160476 A2 | 8/2020 |

OTHER PUBLICATIONS

Chuter et al., "Standardized off-the-shelf components for multi-branched endovascular repair of thoracoabdominal aortic aneurysms," Perspectives in Vascular Surgery and Endovascular Therapy, 23(3):195-201 (2011).

Elkouri et al., "Most patients with abdominal aortic aneurysm are not suitable for endovascular repair using currently approved bifurcated stent-grafts," Vascular and Endovascular Surgery, 38(5):401-412 (2004).

Hazer et al., "A workflow for computational fluid dynamics simulations using patient-specific aortic models," 24th CADFEM Users Meeting 2006, International Congress on FEM Technology with 2006 German ANSYS Conference, Oct. 25, 2006, 9 pages.

Higashiura et al., "Initial experience of branched endovascular graft for abdominal aortic aneurysm with complex anatomy of proximal neck: planning and technical considerations," Jpn J Radiol, 28:66-74 (2010).

International Search Report and Written Opinion dated Apr. 23, 2019 for International Application No. PCT/US2018/052400, 16 pages.

Legget et al., "System for quantitative three-dimensional echocardiography of the left ventricle based on a magnetic-field position and orientation system," IEEE Transactions on Biomedical Engineering, 45(4):494-504 (1998).

Leotta et al., "Measurement of abdominal aortic aneurysms with three-dimensional ultrasound imaging: preliminary report," Journal of Vascular Surgery, 33(4):700-707 (2001).

Malina et al., "EVAR and complex anatomy: an update on fenestrated and branched stent grafts," Scandinavian Journal of Surgery, 97:195-204 (2008).

Nordon et al., "Toward an 'off-the-shelf' fenestrated endograft for management of short-necked abdominal aortic aneurysms: an analysis of current graft morphological diversity," J Endovasc Ther., 17:78-85 (2010).

Oderich et al., "Modified fenestrated stent grafts: device design, modifications, implantation, and current applications," Perspectives in Vascular Surgery and Endovascular Therapy, 21(3):157-167 (2009).

Resch et al., "Incidence and management of complications after branched and fenestrated endographing," Journal of Cardiovascular Surgery, 51(1):105-113 (2010).

(56) References Cited

OTHER PUBLICATIONS

Ricotta et al., "Fenestrated and branched stent grafts." Perspective Vascular Surgery and Endovascular Therapy, 20(2):174-187 (2008).
Stratasys, Dimension 1200es 3D modeling printer, Durability Meets Affordability, www.stratasys.com/3d-printers/design-series/performance/dimension-1200es, 2014, 4 pages.
UK Evar Trial Investigators, "Endovascular versus open repair of abdominal aortic aneurysm," New England Journal of Medicine, 362(20):1863-1871 (2010).

\* cited by examiner

1402 — Disposing a branch stent within a fenestration of a tubular graft such that an engagement portion of the branch stent is aligned with a coupling member disposed about the fenestration, the coupling member being expandable from a first configuration to a second configuration 1404 — Radially expanding the branch stent via an expandable member disposed within the branch stent such that the engagement portion of the branch stent applies an expanding force to the coupling member, the expanding force operable to expand the coupling member from the first configuration to the second configuration 1406 — Removing the expanding force and allowing the coupling member to contract to a third configuration, the coupling member operable to apply a contracting force to the branch stent as the branch stent transitions from the second configuration to the third configuration

SYSTEMS, DEVICES, AND METHODS FOR COUPLING A PROSTHETIC IMPLANT TO A FENESTRATED BODY

CROSS-REFERENCE TO RELATED APPLICATIONS

This application is a continuation of International Patent Application No. PCT/US2018/052400, entitled "Systems, Devices, and Methods for Coupling a Prosthetic Implant to a Fenestrated Body," filed Sep. 24, 2018, which claims priority to and the benefit of U.S. Provisional Patent Application No. 62/562,776, entitled "Systems, Devices, and Methods for Coupling a Prosthetic Implant to a Fenestrated Body," filed Sep. 25, 2017, the disclosures of which are hereby incorporated by reference in their entirety.

BACKGROUND

The embodiments described herein relate generally to prosthetic implants and more particularly to devices and methods for engaging a prosthetic implant, such as, for example, a branch vessel stent graft, within a fenestration of a second prosthetic implant, such as, for example, an aortic stent graft.

Prosthetic devices are often implanted into, for example, diseased portions of a patient to repair, support, stent, and/or otherwise facilitate the proper function of those diseased portions. In some instances, prosthetic devices such as stent grafts can be used to repair diseased portions of a patient's vascular system. For example, aneurysms within a patient's vascular system generally involve the abnormal swelling or dilation of a blood vessel such as an artery, which typically weakens the wall of the blood vessel making it susceptible to rupture. An abdominal aortic aneurysm (AAA) is a common type of aneurysm that poses a serious health threat. A common way to treat AAA and other types of aneurysms is to place an endovascular stent graft in the affected blood vessel such that the stent graft spans across (e.g., traverses) and extends beyond the proximal and distal ends of the diseased portion of the vasculature. The stent graft can, thus, reline the diseased vasculature, providing an alternate blood conduit that isolates the aneurysm from the high-pressure flow of blood, thereby reducing or eliminating the risk of rupture. In other instances, a prosthetic device can be an implant and/or mechanism, which can provide structural or functional support to a diseased and/or defective portion of the body. In some instances, however, the arrangement of the anatomy can present challenges when attempting to place and/or secure a prosthetic device (including stent grafts or the like). Such challenges can result in misalignment and/or suboptimal configuration of the prosthetic device within the anatomy.

Minimally invasive endovascular repair using stent grafts is often preferred to avoid the risks associated with traditional open surgical repair. However, these stent grafts can only be used when the graft can be placed in a stable position without covering major branch vessels. In the cases of juxtarenal aneurysm where the dilation extends up to but does not involve the renal arteries, the proximal portion of the stent graft needs to be secured to the aortic wall above the renal arteries, thereby blocking the openings to the renal arteries. Thus, patients with juxtarenal aneurysms, which represent a significant proportion of abdominal aortic aneurysm cases, are typically excluded from endovascular treatment.

To allow for endovascular repair of a wider range of cases, surgeons sometimes cut openings in the stent graft body to accommodate specific branch vessel origins, a process known as "fenestration". Thus, for example, in treating juxtarenal aneurysms using a procedure known as Fenestrated Endovascular Aortic Repair ("FEVAR"), the fenestrations or openings of an aortic stent graft are to be aligned with the branch vessels. Additional stent grafts (e.g., renal stents) can then be placed in the branch vessels and secured to the primary stent graft (e.g., aortic stent graft) to limit movement of the primary stent grafts within the anatomy and ensure proper blood flow. Additionally, in some cases, an endovascular stent graft can be placed within one or more specific branch vessels to further treat an aneurysm and/or to reinforce the branch vessel in the region of the aneurysm.

SUMMARY

Devices, systems, and methods for implanting a patient-specific prosthesis at a treatment site in a patient are disclosed herein. In some embodiments, a patient-specific prosthesis includes a tubular graft and a coupling member. A fenestration can be disposed in the tubular graft, the fenestration corresponding to a predicted branch blood vessel location. The coupling member can be disposed about the fenestration. The coupling member can include a coil configured to expand from a first configuration to a second configuration in response to the application of an expanding force. The coil can be configured to contract to a third configuration upon removal of the expanding force.

BRIEF DESCRIPTION OF THE DRAWINGS

FIG. 13 is a flow chart illustrating a method of deploying a branch stent, according to an embodiment.

DETAILED DESCRIPTION

Figure 1:
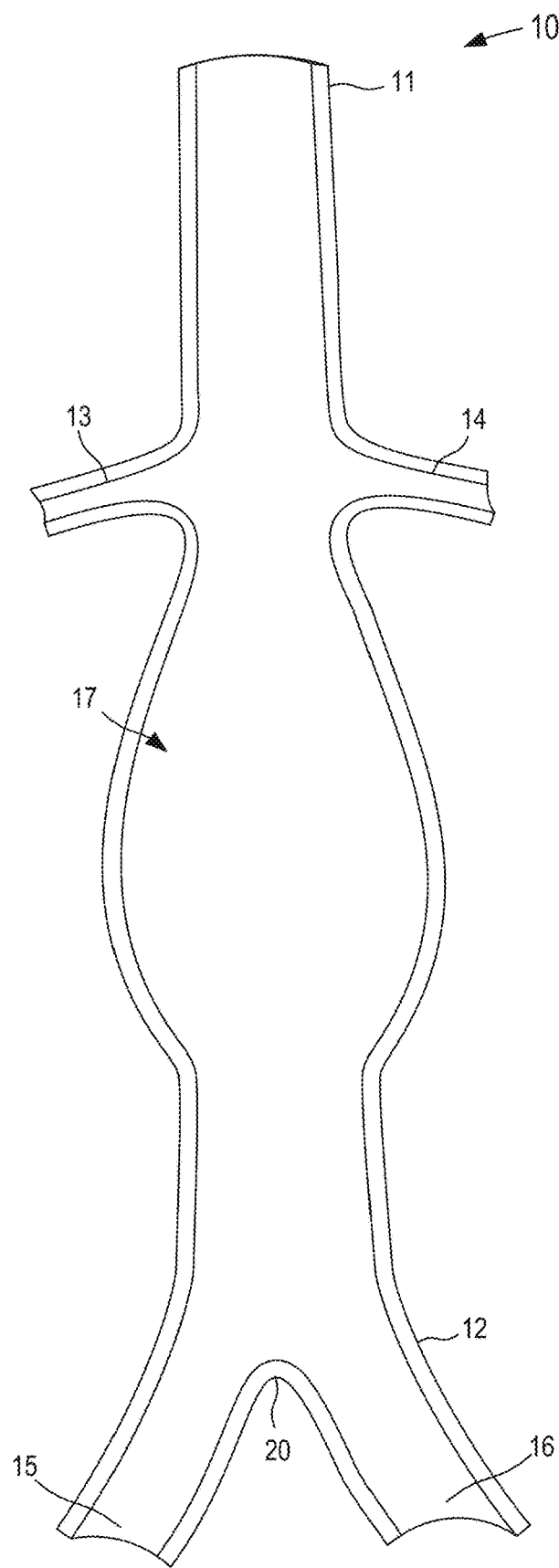
FIG. 1 is an illustration of a diseased abdominal aorta according to an embodiment.

Devices, systems, and methods for implanting a patient-specific prosthesis at a treatment site in a patient are disclosed herein. In some embodiments, a patient-specific prosthesis includes a tubular graft and a coupling member. A fenestration can be disposed in the tubular graft, the fenestration corresponding to a predicted branch blood vessel location. The coupling member can be disposed about the fenestration. The coupling member can include a coil configured to expand from a first configuration to a second configuration in response to the application of an expanding force. The cod can be configured to contract to a third configuration upon removal of the expanding force.

In some embodiments, a patient-specific prosthesis includes a tubular graft, a coupling member, and a branch stent. A fenestration can be disposed in the tubular graft, the fenestration corresponding to a predicted branch blood vessel location. The coupling member can be disposed about the fenestration. The branch stent can be configured to be coupled to the fenestration. The branch stent can include an engagement portion for engaging with the coupling member and a flexible tail portion extending from the engagement portion.

In some embodiments, a system for treating aneurysms includes a tubular graft, a coupling member, a radially expandable branch stent, and an expandable member. A fenestration can be disposed in the tubular graft, the fenestration corresponding to a predicted branch blood vessel location. The coupling member can be disposed about the fenestration, the coupling member configured to expand from a first configuration to a second configuration in response to the application of an expanding force, and contract to a third configuration upon removal of the expanding force. The radially expandable branch stent can be configured to be coupled to the fenestration, the branch stent including an engagement portion for engaging with the coupling member and a flexible tail portion extending from the engagement portion. The expandable member can be configured to transition the radially expandable branch stent from a collapsed configuration to an expanded configuration, the expandable member having a first portion configured to expand the engagement portion of the branch stent, and a second portion configured to expand the flexible tail portion of the branch stent, the first portion configured to have a diameter in an expanded state greater than an inside diameter of the coupling member in the third configuration.

In some embodiments, a method includes disposing a branch stent within a fenestration of a tubular graft such that an engagement portion of the branch stent is aligned with a coupling member disposed about the fenestration. The coupling member can be expandable from a first configuration to a second configuration. The branch stent can be radially expanded via an expandable member disposed within the branch stent such that the engagement portion of the branch stent applies an expanding force to the coupling member. The expanding force can be operable to expand the coupling member from the first configuration to the second configuration. The expanding force can be removed and the coupling member can be allowed to contract to a third configuration. The coupling member can be operable to apply a contracting force to the branch stent as the branch stent transitions from the second configuration to the third configuration.

In some embodiments, an apparatus includes an expandable member. The expandable member can include a first portion and a second portion. The first portion can have a first wall thickness and the second portion can have a second wall thickness. The first wall thickness can be less than the second wall thickness. The first portion can be in fluid communication with the second portion such that an inflation medium provided to at least one of the first portion and the second portion causes both the first portion and the second portion to inflate. The first portion can inflate to a larger diameter than the second portion. The first portion can be configured such that, when the first portion is engaged with a radially expandable stent, an intermediate portion of the first portion can expand into an opening defined by the radially expandable stent such that the expandable member is axially secured relative to the radially expandable stent.

As used in this specification, the singular forms "a," "an" and "the" include plural referents unless the context clearly dictates otherwise. Thus, for example, the term "a member" is intended to mean a single member or a combination of members, "a material" is intended to mean one or more materials, or a combination thereof.

As used herein, the words "proximal" and "distal" refer to a direction closer to and away from, respectively, an operator of, for example, a medical device. Thus, for example, the end of the medical device contacting the patient's body would be the distal end of the medical device, while the end opposite the distal end would be the proximal end of the medical device. Similarly, when a device such as an endovascular stent graft is disposed within a portion of the patient, the end of the device closer to the patient's heart would be the proximal end, while the end opposite the proximal end would be the distal end. In other words, the proximal end of such a device can be upstream of the distal end of the device.

The embodiments described herein can be formed or constructed of one or more biocompatible materials. Examples of suitable biocompatible materials include metals, ceramics, or polymers. Examples of suitable metals include pharmaceutical grade stainless steel, gold, titanium, tantalum, tungsten, nickel, iron, platinum, tin, cobalt, chromium, copper, and/or alloys thereof. Examples of polymers include nylons, polyesters, polycarbonates, polyacrylates, polymers of ethylene-vinyl acetates and other acyl substituted cellulose acetates, non-degradable polyurethanes, polystyrenes, polyvinyl chloride, polyvinyl fluoride, poly (vinyl imidazole), chlorosulphonate polyolefins, polyethylene oxide, polyethylene terephthalate (PET), polytetrafluoroethylene (PTFE), urethanes, and/or blends and copolymers thereof.

The embodiments and methods described herein can be used to form a patient-specific prosthetic device and/or to facilitate the function and/or the integration of the prosthetic device within a portion of a patient. For example, in some embodiments, the devices and/or methods described herein can be used in conjunction with and/or can otherwise be included in endovascular repair using stent grafts. Although the embodiments are shown and described herein as being used, for example, to facilitate endovascular repair, in other embodiments, any of the devices and/or methods described herein can be used to facilitate treatment of any portion of a patient. For example, the devices and methods described herein can form and/or can facilitate the integration of any suitable implant, prosthesis, device, mechanism, machine, and/or the like within a portion of the body of a patient such as the patient's vascular system, nervous system, muscularskeletal system, etc. Therefore, while some embodiments are shown and described herein as being used in the endovascular repair of an abdominal aortic aneurysm, they are presented by way of example and are not limited thereto.

Some of the devices and/or methods described herein can be used in minimally invasive treatment techniques such as endovascular repair using stent grafts. Such repair techniques are generally preferred over traditional open surgical repair and often result in reduced morbidity or mortality rates. In some instances, however, the arrangement of the diseased vasculature can result in a need to alter a portion of the stent graft prior to insertion into the body. For example, in an endovascular repair of an abdominal aortic aneurysm, the aneurysm can be situated adjacent to and/or directly distal to normally functioning vessels branching from a portion of the aorta. In order to reline the aneurysm with the stem graft, surgeons or manufacturers often cut openings in the stent graft fabric to accommodate specific branch vessel origins, a process known as "fenestration." Specifically, in treating juxtarenal aneurysms and/or when treating other aneurysms, shown in illustration in FIG. 1 for instance, the fenestrations or openings of the stent grafts can correspond to a size, shape, and/or relative position of, inter alia, the renal arteries, the superior mesenteric artery (SMA), and/or the celiac artery (not shown in the illustration in FIG. 1).

Traditionally, the fenestration process involves measurements based on medical images (such as CT scans) of the vessel origins. For example, in some instances, longitudinal distances of branch vessels can be measured and relative angular locations of the branch vessels can be estimated and/or calculated from a reference point. Based on these measurements and/or calculations, a surgeon or manufacturer can mark and cut the stent fabric of a stent graft to define one or more fenestrations. The fenestrated stent graft can then be positioned within the diseased vasculature (e.g., via an endovascular procedure) and oriented to substantially align the fenestrations with openings of the corresponding branch vessels.

In some instances, fenestrations in the fenestrated bodies (e.g., fenestrated stent grafts or vessel walls) described herein can be generated and/or otherwise formed based on medical imaging data of a diseased portion of a patient's vascular system (e.g., an abdominal aortic aneurysm). For example, an electronic device such as a personal computer, workstation, laptop, etc, can receive the imaging data and can calculate and/or otherwise define a digital representation of the imaging data. Based on the digital representation, the electronic device can define one or more templates, process plans, instructions, data sets, and/or the like associated with and/or indicative of a desired set of fenestration locations along a body (e.g., a stent graft). In some instances, the electronic device can output a map, plan, and/or template, which in turn, can be used by a doctor, surgeon, technician, and/or manufacturer to form a fenestrated body (e.g. a fenestrated stent graft). For example, in some embodiments, such a template or the like can be substantially similar to those described in U.S. Patent Publication No. 2013/0296998 entitled, "Fenestration Template for Endovascular Repair of Aortic Aneurysms," filed May 1, 2013 ("the '998 publication") and/or those described in U.S. patent application Ser. No. 15/163,255 entitled, "Devices and Methods for Anatomic Mapping for Prosthetic Implants," filed May 24, 2016 ("the '255 application"), the disclosures of which are incorporated herein by reference in their entireties.

In other instances, fenestrations in the fenestrated bodies (e.g. a fenestrated stent grafts or vessel walls) can be formed without such templates. For example, in some embodiments, the electronic device can output instructions and/or code (e.g., machine code such as G-code or the like) to a computerized numerical control (CNC) device and/or a computer-aided manufacturing (CAM) device, which in turn, can perform one or more manufacturing processes or the like associated with forming and/or otherwise marking fenestration locations along a patient-specific prosthesis (e.g., a stent graft). The formation of a patient-specific prosthesis can be performed in a manual process or in at least a partially, automated process. Moreover, a change in the arrangement of a portion of the anatomy resulting from the insertion and/or indwelling of the prosthesis can be determined and/or calculated using the devices and/or methods described in International Patent Application No. PCT/US2016/041355, entitled "Devices and Methods for Anatomic Mapping for Prosthetic Implants," filed Jul. 7, 2016 ("the '355 application"), the disclosure of which is incorporated herein by reference in its entirety.

Figure 2A:
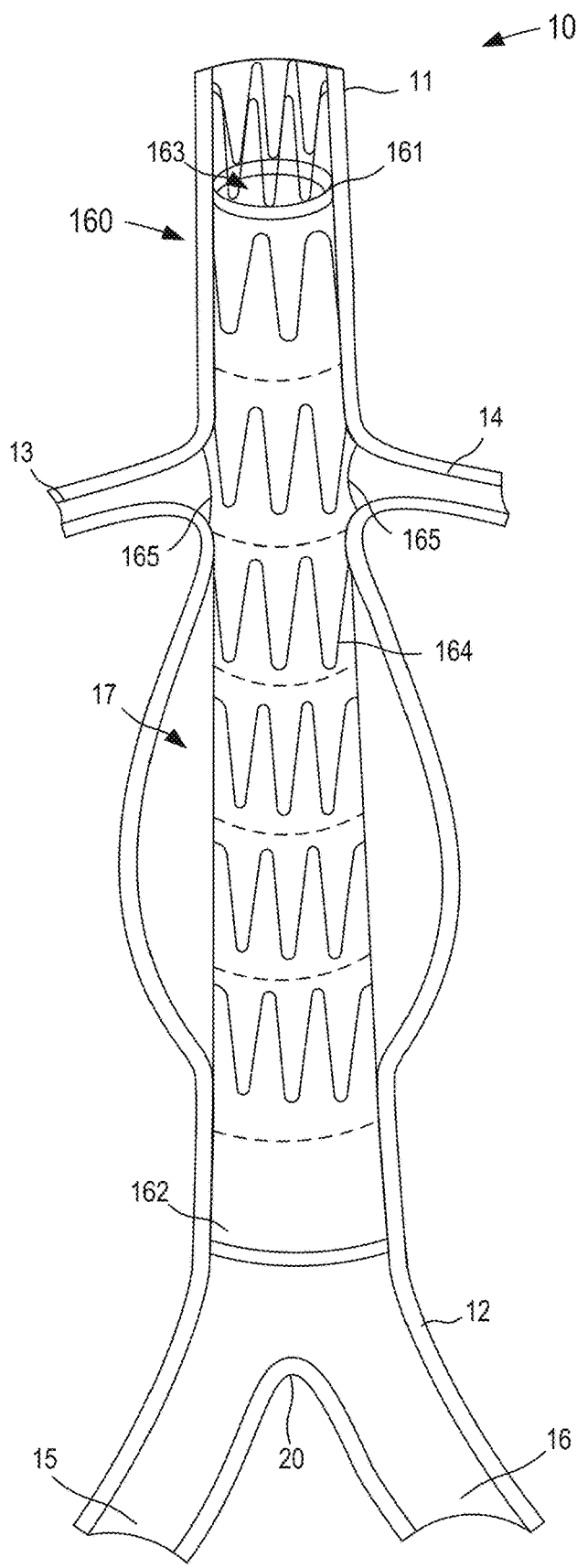
FIG. 2A is a portion of a stent graft according to an embodiment and directly after placement within the diseased abdominal aorta of FIG. 1.
Figure 2B:
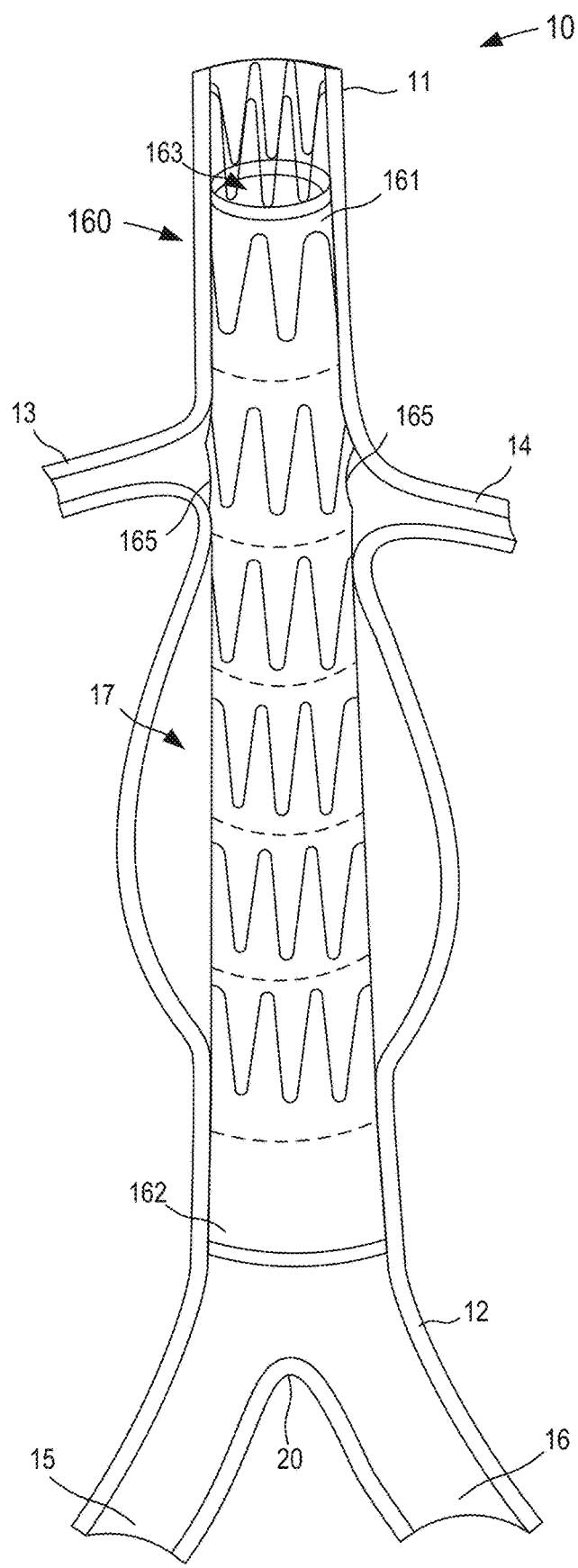
FIG. 2B is a portion of the stent graft of FIG. 2A and placed within the diseased abdominal aorta of FIG. 1 and after a time of indwelling.

FIGS. 1-2B illustrate a diseased portion of a patient's abdominal aorta 10. While portions of the abdominal aorta 10 are described below, the discussion of the abdominal aorta 10 is not exhaustive; rather, the discussion below provides a reference to the relevant anatomic structures. Moreover, the discussion of the anatomic structures e.g., of the abdominal aorta 10) refers to the position, orientation, etc. of such structures relative to the patient rather than as viewed by an observer (e.g., a doctor). For example, when referring to a "left" side of a patient or to anatomic structures disposed on or near the "left" side of the patient, "left" is intended to describe a position relative to the patient and/or from the patient's perspective, as viewed in an anterior direction (e.g., forward).

The abdominal aorta 10 (also referred to herein as "aorta") has a proximal end portion 11, receiving a flow of blood from the descending aorta (not shown), and a distal end portion 12, supplying a flow of blood to the lower limbs. As shown in FIG. 1, the aorta 10 at or near the proximal end portion 11 supplies a flow of blood to the right renal artery 13 and the left renal artery 14, which in turn, supply blood to the right and left kidney (not shown), respectively. Although not shown in FIG. 1, the proximal end portion 11 of the aorta 10 also supplies a flow of blood to the superior mesenteric artery (SMA) and the celiac artery. The distal end portion 12 of the aorta 10 forms the iliac bifurcation 20, through which the aorta 10 supplies a flow of blood to the right common iliac artery 15 and the left common iliac artery 16, which in turn, supply blood to the right and left lower limbs, respectively. As shown in FIG. 1, this patient has an abdominal aortic aneurysm (AAA) 17 positioned distal to the renal arties 13 and 14 and proximal to the iliac bifurcation 20. More specifically, the AAA 17 is disposed in a position that precludes the attachment of a proximal end portion of a stent graft between the renal arteries 13 and 14 and the AAA 17, and thus, a fenestrated stent graft 160 (see e.g., FIGS. 2A and 2B) is used for endovascular repair of the AAA 17.

In some instances, endovascular repair of the AAA 17 includes scanning and/or otherwise capturing anatomic imaging data associated with the patient's aorta 10. For example, an imaging device can be an X-ray device, a computed tomography (CT) device, a computed axial tomography (CAT) device, a magnetic resonance imaging device (MRI), a magnetic resonance angiogram (MRA) device, a positron emission tomography (PET) device, a single photon emission computed tomography (SPECT) device, an ultrasound device, and/or any other suitable device for imaging a portion of the patient and/or a combination thereof (e.g., a CT/MRA device, a PET/CT device, a SPECT/CT device, etc. The imaging data captured by the imaging device can thus, be used to determine salient features of the patient's aorta 10 such as, for example, the branch vessels in fluid communication with the aorta 10. For example, a doctor, surgeon, technician, manufacturer, etc. can use the imaging data to determine and/or calculate a size, shape, position, and/or orientation of the aorta 10, the branch vasculature in fluid communication with the aorta 10 (e.g., the renal arteries 13 and 14), and/or any other suitable vasculature or anatomic structure. In some instances, the doctor, surgeon, technician, manufacturer, etc. can form and/or define one or more fenestrations 165 in the stent graft 160 associated with the determined and/or calculated characteristics of at least the renal arteries 13 and 14, as described in the '998 application, the '255 application, and/or the '355 application, incorporated by reference above.

As shown in FIG. 2A, the stent graft 160 can be positioned within a portion of the patient's abdominal aorta 10 via an endovascular procedure. For example, the stent graft 160 can be disposed within a delivery catheter (e.g., in a collapsed, compressed, restrained, and/or otherwise un-deployed configuration), which is inserted into, for example, the femoral artery (not shown). The delivery catheter can be advanced through the artery and into the abdominal aorta 10. Once advanced to a desired position within the abdominal aorta 10, the delivery catheter can be withdrawn relative to the stent graft 160. As the delivery catheter is retracted and/or withdrawn, the stent graft 160 transitions from the collapsed configuration to an expanded or deployed configuration, thereby stenting a portion of the abdominal aorta 10.

The stent graft 160 includes a proximal end portion 161 and a distal end portion 162 and defines a lumen therethrough 163. The stent graft 160 can be any suitable stent graft. For example, the stent graft 160 can be formed from a resilient, biocompatible material such as those described above. For example, a stent graft can include a stent or framework to which a graft material is coupled. In some embodiments, the stent (i.e., framework) can be constructed from a metal or metal alloy such as, for example, nickel titanium (nitinol) and the graft material can be constructed from a woven polymer or fabric such as, for example, polytetrafluoroethylene (PTFE) or polyethylene terephthalate (PET or Dacron®). In some embodiments, the graft material or fabric can be woven onto the stent and/or coupled to the stent in any other suitable manner to form the stent graft (e.g., the stent graft 160).

The stent graft 160 also includes a set of stiffening members 164 disposed circumferentially about the stent graft 160. The stiffening members 164 can be any suitable structure that can, for example, bias the stent graft 160 in an open configuration, thereby structurally supporting the stent graft material (also known as "stent fabric" or "graft fabric"). In some embodiments, the stiffening members 164 can be formed from a metal or a metal alloy such as, for example, those described above. In some embodiments, such a metal or metal alloy, for example, is radiopaque and/or otherwise coated with a radiopaque material configured to be visible using, for example, fluoroscopy. The stiffening members 164 can transition from a restrained or deformed delivery configuration (e.g., when disposed in a delivery catheter) to an expanded and/or biased indwelling configuration, as shown in FIG. 2A.

In this embodiment, the stent graft 160 defines the set of fenestrations 165, as described above. As described herein, the position of the fenestrations 165 along the stent graft 160 can be based on anatomic imaging data and/or one or more digital representations of the patient's anatomy. A doctor, surgeon, technician, and/or manufacturer can then use the imaging data and/or digital representations to define the fenestrations 165 in the graft fabric. As shown, in this example, the fenestrations 165 are each aligned with its corresponding renal artery 13 or 14 and can each have a size, shape, and/or configuration that is associated with its corresponding renal artery 13 or 14. In this manner, the fenestrations 165 can allow blood to flow from the aorta 10 and into the right renal artery 13 and the left renal artery 14 via the fenestrations 165. Although not shown in FIG. 2A, the stent graft 160 can define one or more fenestrations associated with other branch vessels stemming from the aorta 10 such as, for example, the superior mesenteric artery (SMA), the celiac artery, and/or the like.

As shown in FIG. 2B, the placement and/or indwelling of the stent graft 160 within the aorta 10 can, for example, alter, shift, rotate, translate, morph, and/or otherwise reconfigure the arrangement of the patient's aorta 10. As a result, the openings of the renal arteries 13 and 14 are shifted relative to the fenestrations 165 defined by the stent graft 160. In some instances, the shifting of the aorta 10 relative to the stent graft 160 results in at least a partial blockage of the renal arteries 13 and 14, as shown in FIG. 2B. For example, in some instances, the openings of the renal arteries 13 and 14 can be about 4 millimeters (mm) to about 7 mm, and the shifting and/or rearrangement of the aorta 10 can result in a shifting of the openings of the renal arteries 13 and 14 relative to the fenestrations 165 by about 1 mm, about 2 mm, about 3 mm, about 4 mm, about 5 mm, about 6 mm, about 7 mm, or more (or fraction of a millimeter there between). Thus, despite defining the fenestrations 165 in desired positions along the stent graft 160 based on the imaging data, the shifting of the aorta 10 resulting from the placement and/or indwelling of the stent graft 160 can result in a blockage of the renal arteries 13 and 14. In some instances, the shifting of the aorta 10 can result in about a 1%, 5%, 10%, 20%, 30%, 40%, 50%, 60%, 70%, 80%, 90%, or 100% (or any percent or fraction of a percent there between) blockage of the renal arteries 13 and 14. Although not shown in FIGS. 2A and 2B, the shifting of the aorta 10 can result in a similar misalignment of any branch vessel relative to its corresponding fenestration in the stent graft 160. In some embodiments, an electronic device can be configured to determine and/or calculate the shift in the anatomy that would result from the insertion and/or indwelling of prosthesis (e.g., a stent graft) and can define one or more digital representations of the shifted anatomy. One or more fenestrations can be formed in a stent graft (e.g., the stent graft 160) based on the calculated shift, as described in the '998 application, the '255 application, and/or the '355 application, incorporated by reference above.

Figure 3:
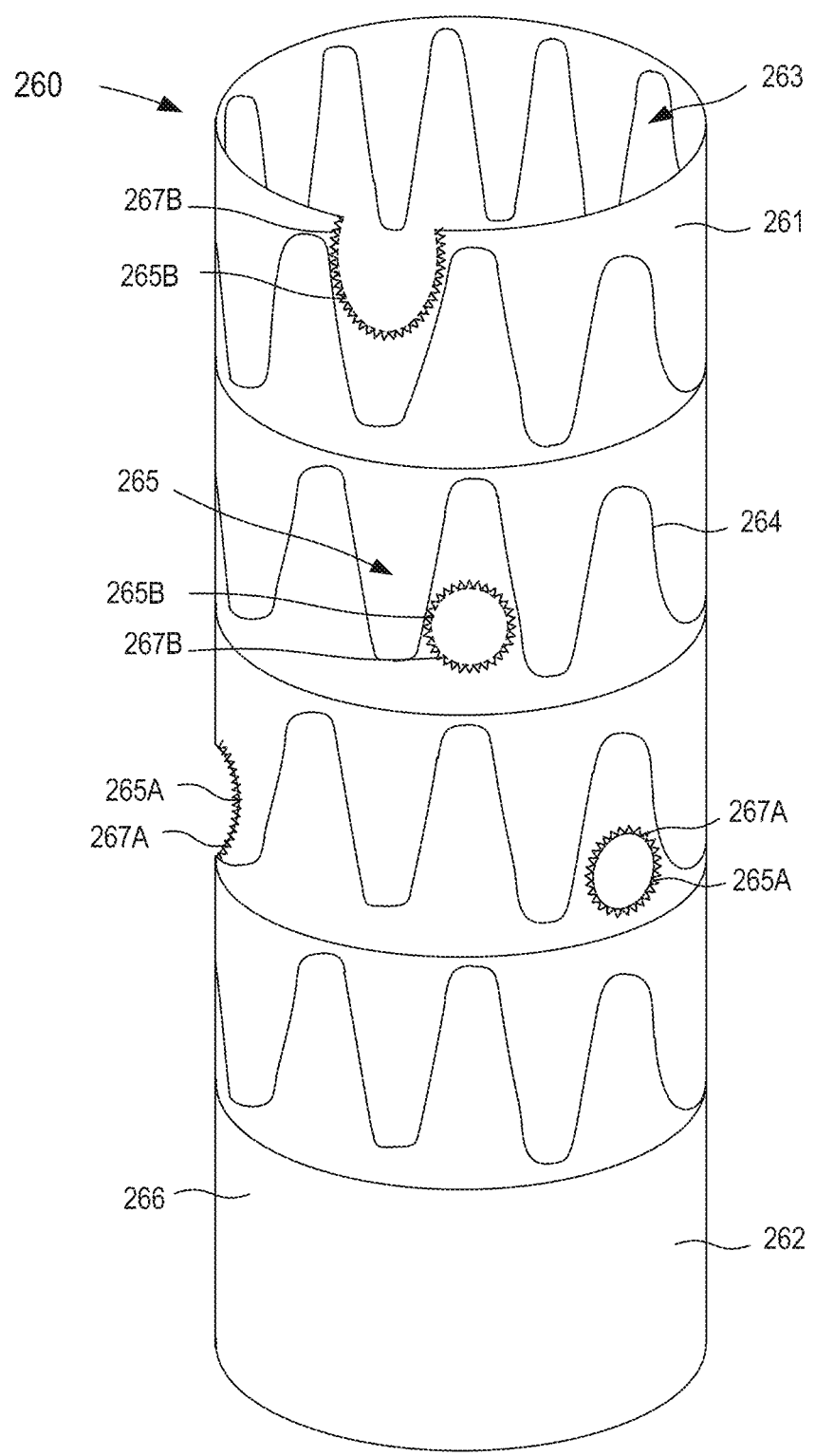
FIG. 3 is an illustration of at least a portion of a fenestrated stent graft according to an embodiment.

FIG. 3 illustrates at least a portion of a fenestrated stent graft 260 according to an embodiment. As described above, a stent graft can define one or more fenestrations configured to accommodate one or more branch vessels when the stent graft is deployed in an aorta. Specifically, in this embodiment, the fenestrated stent graft 260 includes a proximal end portion 261 and a distal end portion 262, and defines a lumen 263 and a set of fenestrations 265. The fenestrated stent graft 260 can be any suitable stent graft and/or prosthesis. For example, in some embodiments, the fenestrated stent graft 260 can be an off-the-shelf stent graft. In other embodiments, the fenestrated stent graft 260 can be a patient-specific stent graft with a size, shape, and/or configuration corresponding to the patient's anatomy.

The fenestrated stent graft 260 (also referred to herein as "stent graft") can have any suitable shape, size, and/or configuration. For example, in some embodiments, the stent graft 260 can have a size that is associated with a size of the lumen defined by the aorta. In other embodiments, the fenestrated stent graft 260 can have a size that is associated with an adjusted or calculated size of the lumen defined by the aorta resulting from the endovascular placement of the stent graft 260. Moreover, the stent graft 260 can have any suitable mechanical properties such as, for example, strength, stiffness, etc.

As shown in FIG. 3, in some embodiments, the stent graft 260 can include stent 264 and a graft fabric 266. The stent 264 can be, for example, any suitable stent and/or framework configured to increase a stiffness of the stent graft 260 and/or to provide structural support for the stent graft 260. As described above, the stent 264 can be formed from any suitable metal or metal alloy such as Nitinol. In some embodiments, the stent 264 can be configured to transition between a first, expanded and/or implanted configuration and a second, collapsed, and/or delivery configuration. Furthermore, in some instances, the stent 264 can be biased such that the stent 264 is in the first configuration until a force is exerted on the stent 264 to transition it from the first configuration to the second configuration (e.g., when disposed in a delivery cannula or the like).

The graft fabric 266 can be formed from any suitable polymer or fabric such as, for example, Dacron® or the like. In some embodiments, the graft fabric 266 can be woven around and/or through the stent 264. In other embodiments, the graft fabric 266 can be coupled to the stent 264 via sutures, a friction fit, or an adhesive, and/or can encapsulate the stent 264 between at least two layers of graft fabric 266. As shown in FIG. 3, the graft fabric 266 defines the fenestrations 265, which can be arranged relative to the stent 264 such that the fenestrations 265 do not overlap the stent 264. In other words, the fenestrations 265 can be arranged along the stent graft 260 such that one or more portions of the stent 264 do not span and/or otherwise traverse the fenestrations 265. In other embodiments, one or more portions of the stent 264 can span and/or otherwise traverse the fenestration 265. Moreover, as described in detail above, the fenestrations 265 can be defined by the graft fabric 266 at locations along the stent graft 260 based on an updated, projected, anticipated, and/or otherwise calculated digital representation of a portion of a patient's vasculature.

As described above, the stent graft 260 can be any suitable stent graft and can be formed via any suitable manufacturing process or processes. In some embodiments, the stent graft 260 can be manufactured as an off-the-shelf stent graft and the fenestrations 265 can be formed in the graft material 266 in a subsequent manufacturing process. In other embodiments, the stent graft 260 can be manufactured as a "custom" or not-off-the-shelf stent graft. While specific methods of manufacturing are described herein, it is to be understood that the methods are presented by way of example only and not limitation. Moreover, the methods of manufacturing described herein can be performed at a single facility and/or in a single manufacturing process or can be performed at multiple facilities and/or in multiple manufacturing processes. In some instances, portions of the methods of manufacturing described herein can be performed by an end user such as a doctor, surgeon, technician, nurse, etc. Thus, while the manufacturing of the stent graft 260 is specifically described below, the stent graft 260 can be formed via any suitable manufacturing process or processes and is not limited to those discussed herein.

In some instances, the stent graft 260 can be manufactured with a general shape, diameter, length, etc. associated with a patient's aorta based on, for example, calculations from anatomic imaging data of the patient. In other embodiments, the stent graft 260 can have a general shape, size, and/or configuration associated with the updated model defined by the electronic device, which in turn, corresponds to a calculated, projected, and/or modified arrangement of the aorta in response to the insertion and indwelling of, for example, the stent graft 260, as described in detail above. Hence, a stent graft 260 generally has a tubular or cylindrical shape. In some embodiments, the diameter of the lumen 263 is at least partially based on a diameter of the calculated, projected, and/or modified lumen defined by the aorta. Moreover, the stent graft 260 can have a stiffness and/or any other suitable mechanical properties associated with an anticipated amount and/or method of shifting of the aorta resulting from the insertion and/or indwelling of the stent graft 260, as described in the '998 application, the '255 application, and/or the '355 application, incorporated by reference above.

The fenestrations 265 can be defined along the stent graft 260 such that each fenestration 265 corresponds to a calculated position of the corresponding branch vasculature such as, for example, the renal arteries, and each fenestration 265 can be formed in any suitable manner, as described in the '998 application, the '255 application, and/or the '355 application, incorporated by reference above.

Figure 4:
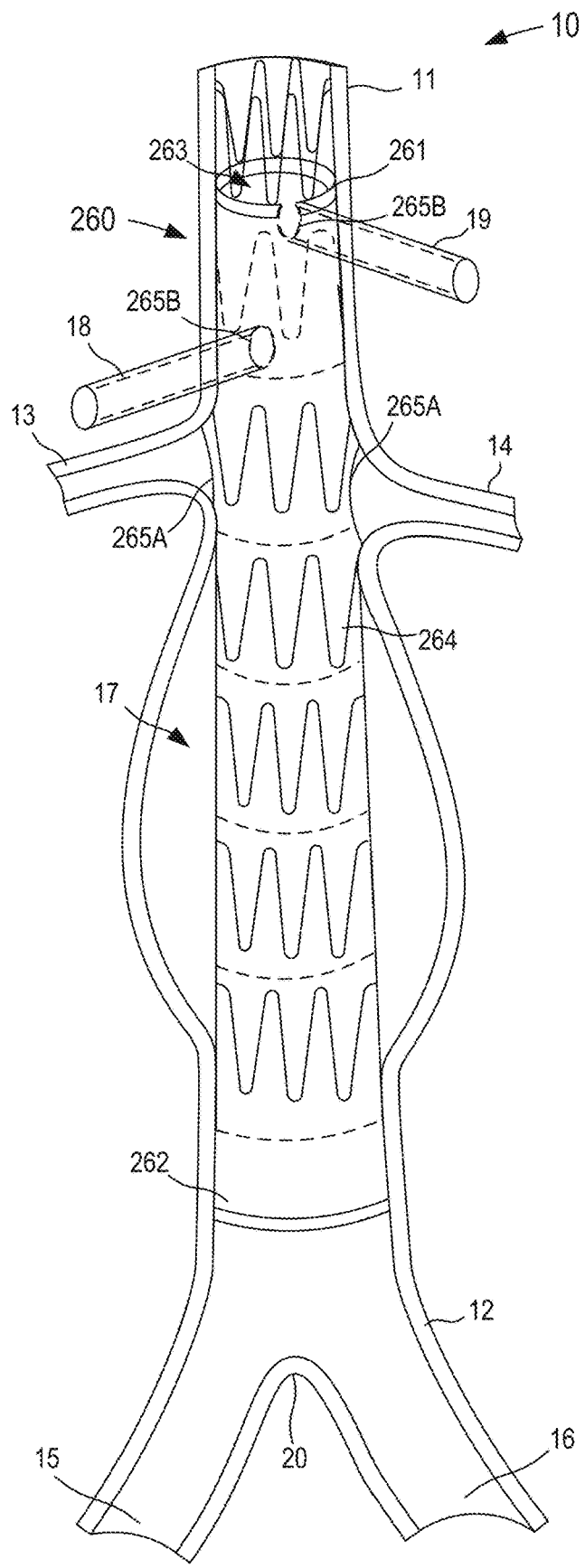
FIG. 4 is an illustration of the portion of the fenestrated stent graft of FIG. 3 positioned, for example, within a portion of a diseased abdominal aorta.

As shown in FIG. 4, when the fenestrations 265 are defined along the stent graft 260, the stent graft 260 can be positioned within a portion of the patient's body using any suitable endovascular procedure. In this embodiment, the stent graft 260 is positioned within the patient's aorta 10. As shown, the stent graft 260 can include, for example, a first set of fenestrations 265A, which are associated with and/or otherwise correspond to the right renal artery 13 and the left renal artery 14. Specifically, each of the fenestrations 265A are aligned with its corresponding renal artery 13 or 14 and can each have a size, shape, and/or configuration that is associated with its corresponding renal artery 13 or 14. In some embodiments, the size, shape, and/or position of the fenestrations 265A is associated with and/or substantially corresponds to the adjusted and/or calculated size, shape, and/or position of its corresponding renal artery 13 and 14. For example, placing the stent graft 260 within aorta 10 can, for example, alter, shift, rotate, translate, morph, and/or otherwise reconfigure the arrangement of the patient's aorta 10. Thus, by basing the stent graft 260 off of the updated model, the size, shape, and/or position of the fenestrations 265 defined by the stent graft 260 can correspond to the desired branch vasculature (e.g., the right renal artery 13 and/or the left renal artery 14). Moreover, in addition to positioning the stent graft 260 within a portion of the patient's aorta 10, the renal arteries 13 and/or 14 can also be stented, for example, through the fenestrations 265A (not shown in FIG. 4). Stenting of the renal arteries can be carried out with secondary branch stents (not shown in FIG. 4) that engage with the fenestrated body of the stent graft 260 at the fenestrations 265A and extend within branch arteries like the renal arteries 13 and/or 14. As such, the fenestrations 265A on the stent graft 260 and the secondary branch stents (not shown) positioned to correspond to the branch arteries can help with the axial and/or radial alignment and positioning of the stem graft 260 during deployment. Further the fenestrations 265A and the secondary branch stents (not shown) can also help maintain the alignment and positioning of the stent graft 260 relative to the patient's aorta 10 after placement.

As shown in FIGS. 3 and 4, in some embodiments, the stent graft 260 can include a second set of fenestrations 265B, which are associated with and/or otherwise correspond to other branch vessels that otherwise, might be blocked by an un-fenestrated portion of the stent graft 260. For example, the fenestrations 265B can be associated with and/or otherwise correspond to the superior mesenteric artery (SMA) 18 and the celiac artery 19, respectively. In other embodiments, the stent graft 260 can define fenestrations to accommodate more or fewer branch vessels than illustrated here. For example, in some embodiments, the stent graft 260 can define fenestrations to accommodate the inferior mesenteric artery (IMA), internal iliac arteries, and/or the like. Thus, the fenestrations 265 defined by the stent graft 260 can allow blood to flow from the aorta 10 to the branch vasculature, which would otherwise be obstructed by the stent graft 260 material.

In some embodiments, the arrangement of the stent graft 260 and/or the patient's aorta can be such that a fenestration 265 is partially defined by the stent graft 260. For example, as shown, the proximal most fenestration 265B is disposed at the proximal end of the stent graft 260 and corresponds to the celiac artery 19 that is partially covered by the graft material during deployment. As such, the fenestration 265B for the celiac artery 19 is partially circular or U-shaped to accommodate the portion of the celiac artery 19 otherwise blocked by the graft material. In other embodiments, any of the fenestrations 265 can have non-circular and/or irregular shapes.

In some embodiments, the fenestrations 265 can be marked to facilitate location of the fenestrations 265 during deployment of the stent graft 260 and to facilitate the coupling of branch stents (not shown) with the stent graft 260. For example, the peripheral edges 267A or 267B of the stent graft 260 that define the fenestrations 265A or 265B may be sutured using gold wires and/or wires of other radiopaque materials. Similarly, the location of the fenestration 265 can be marked by one or more radiopaque markers. Such radiopaque wires or markers can facilitate fluoroscopic visualization of the fenestrations 265 during an endovascular repair procedure and allow a physician to locate the fenestration 265 with respect to the corresponding branch vessel. In other embodiments, the fenestrations 265 can be sutured and/or otherwise marked using any suitable material that can increase visibility, for example, when using any suitable imaging device (e.g., MRI scan, CAT scan, PET scan, X-Ray scan, ultrasound, etc.). Such markers can be placed and/or sutured in any suitable manufacturing process, which can be combined with or separate from the formation of the fenestrations 265.

As described above, in some embodiments, a secondary branch stent can be coupled within a fenestration (e.g., fenestrations 265) of a stent graft (e.g., stent graft 260). The relative position of the secondary branch stent can help in the axial and radial alignment and/or positioning of the stent graft 260 with respect to the patients aorta 10 during deployment. During placement of the stent graft the secondary stent can be disposed within a branch vessel (e.g., the SMA 18) extending from a patient's aorta such that the secondary stent can aid in reinforcing the branch vessel in an open position. Additionally, the secondary stent may help maintain the axial and/or radial positioning of the stent graft relative to the patient's aorta (e.g., aorta 10) after placement. The secondary stent may be movable within and/or relative to the fenestration such that a motion of the branch vessel can be accommodated (i.e., vessel tortuosity can be compensated for and vessel kinking can be prevented). In some embodiments, a fenestrated body, such as a main stent graft, can include a flexible portion surrounding a fenestration such that a rigid branch stent engaged with the fenestrated body at the fenestration can rotate within the fenestration. For example, FIG. 5A is a schematic illustration of a cross-sectional view of an assembly 300. The assembly 300 includes a fenestrated body 360, a branch stent graft 330 (also referred to herein as a "branch stent"), a radially expandable coupling member 320, and an expandable member 340. The fenestrated body 360 can be, for example, a tubular graft and/or a main stent graft, such as an aortic stent graft. The fenestrated body 360 can have the same or similar structure and/or function as any of the other fenestrated bodies or stent grafts described herein, such as, for example, stent graft 160 or stent graft 260. The fenestrated body 360 can define a fenestration 365 and include an engagement portion 368 surrounding the fenestration 365. The fenestration 365 can correspond to a predicted branch blood vessel location.

The coupling member 320 can be coupled to the fenestrated body 360 such that the coupling member 320 is disposed about the fenestration 365. For example, the coupling member 320 can partially or completely surround the fenestration 365. The coupling member 320 can include, for example, a coil (not shown). The coil can include a radiopaque material such that the coil can be viewed using radiographic imaging. The radiopaque material can include tungsten, platinum, gold, tantalum, and/or any other suitable radiopaque material. In some embodiments, the coil can have a spring rate of at least about 0.025 N/mm. In some embodiments, the cod can have a first end and a second end, and the first end can be coupled to the second end (e.g., via welding) to form a ring.

The coupling member 320 can be coupled to the fenestrated body 360 via any suitable coupling mechanism. For example, the coupling member 320 can be stitched to the fenestrated body 360 using, for example, sutures. In some embodiments, the coupling member 320 can be coupled to the fenestrated body 360 via polyurethane. In some embodiments, the coupling member 320 can be coupled to the fenestrated body 360 via a mechanical coupling, via welding, or via any apparatus or method described in International Application No. PCT/US2017/037157, filed Jun. 13, 2017, entitled "Systems, Devices, and Methods for Marking and/or Reinforcing Fenestrations in Prosthetic Implants" (referred to herein as the '157 application), which is hereby incorporated by reference in its entirety.

The coupling member 320 can be configured to expand from a first configuration having a first diameter (e.g., D1) to a second configuration having a second diameter (e.g., D2 shown in FIG. 5B) in response to the application of an expanding force, such as an expanding force applied by the expandable member 340. After expanding, the coupling member 320 can be configured to contract from the second configuration to a third configuration having a third diameter (e.g., D3 shown in FIG. 5C) upon removal of the expanding force. Additionally, the coupling member 320 can be configured to engage with the branch stent graft 330. For example, the expandable member 340 can be expanded such that the expandable member 340 applies an expanding force to an inner wall of the branch stent graft 330, causing an outer wall of the branch stent graft 330 to contact, engage with, and/or expand the coupling member 320 from the first configuration to the second configuration, as described in more detail below with reference to FIGS. 5A-5D.

In some embodiments, the coupling member 320 can optionally include a shape memory core (not shown) disposed in the coil (e.g., within a central lumen of the coil). The shape memory core can include a shape memory material or structure such that the shape memory core can revert to a predetermined shape (e.g., a circular shape). For example, the coupling member 320 can include a shape memory material such that the coupling member 320 can revert to a circular shape after being collapsed or compressed for delivery to a particular vascular location via a delivery sheath. The shape memory core can also prevent kinking of the coil during the collapsing, delivery, and expansion of the coil at the desired vascular location. In some embodiments, the shape memory core can include a shape memory alloy, such as, for example, Nitinol (i.e., nickel titanium). In some embodiments, the shape memory core can be shaped such that it forms an incomplete or broken ring (i.e., not a complete or closed ring). In some embodiments, the shape memory core can be shaped as a split key ring. Thus, when the coupling member 320 expands, the shape memory core can also expand and the ends of the shape memory core within the coupling member 320 can separate. When the coupling member 320 contracts to a smaller diameter, the shape memory core can also contract and the ends of the shape memory core can approach each other. In some embodiments, the coil in combination with the shape memory core can have a spring rate of at least about 0.025 N/mm. In some embodiments, the coil alone (i.e., without the shape memory core) can have a spring rate of at least about 0.025 N/mm.

Figure 5B:
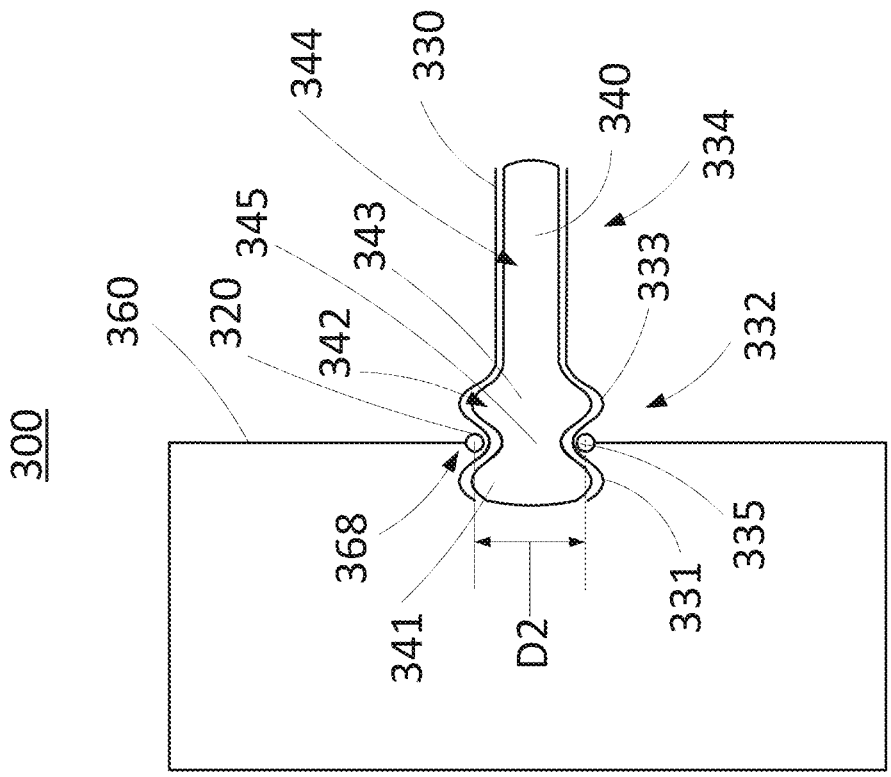
FIGS. 5A-5D are schematic illustrations of a cross-sectional view of an assembly in a variety of configurations, according to an embodiment.
Figure 5A:
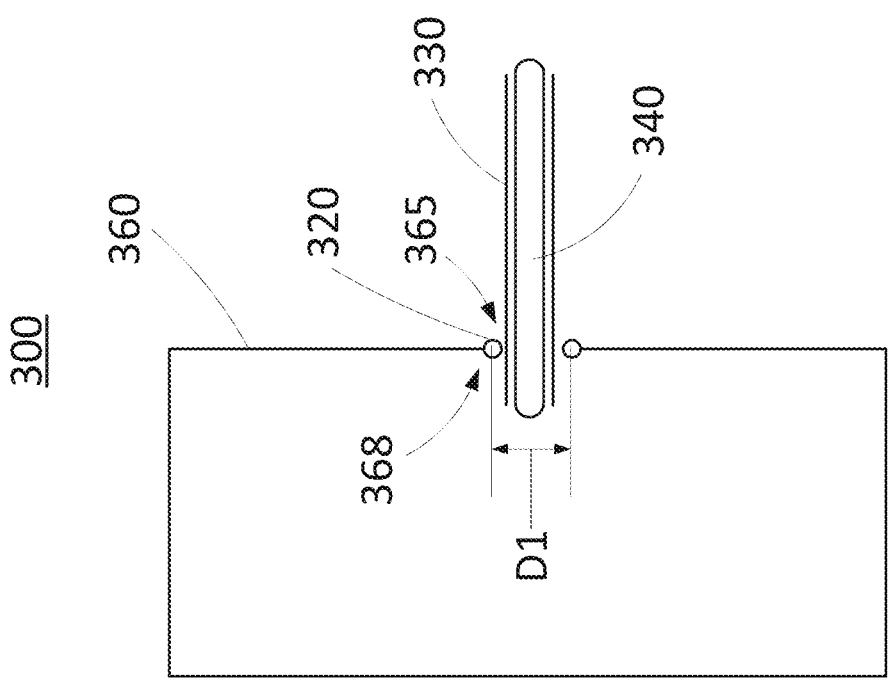
Figure 5D:
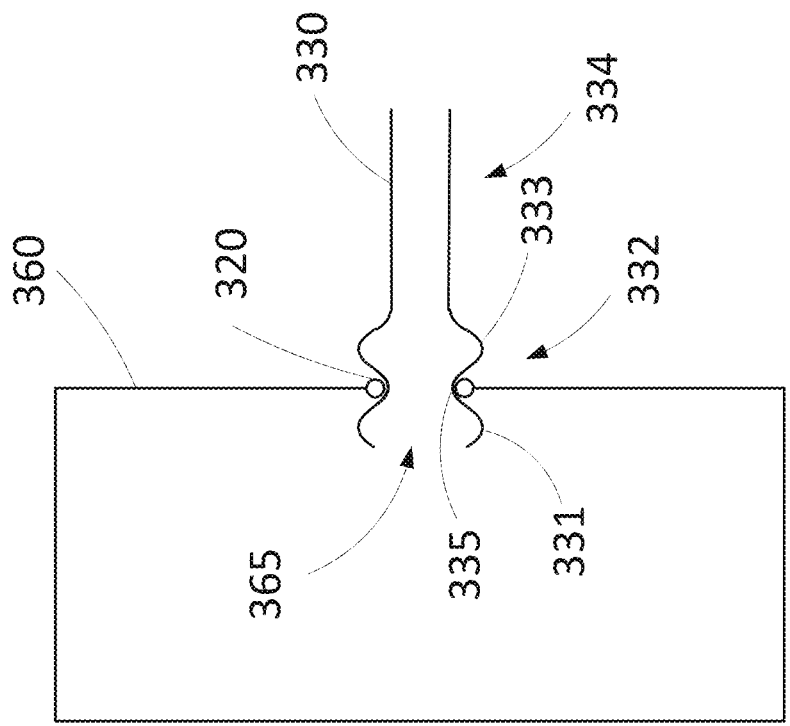

The branch stent 330 can be expandable from an initial, contracted configuration (shown in FIG. 5A) to an expanded configuration (shown in FIG. 5B). The branch stent 330 or a portion of the branch stent (e.g., an engagement portion 332 described below) can also be able to be contracted from the expanded configuration to a final, contracted configuration (shown in FIG. 5C). As identified in FIG. 5B and described in more detail with reference to branch stent 730 shown in FIG. 9, the branch stent 330 can include an engagement portion 332 and a flexible tail portion 334 extending from the engagement portion 332. In some embodiments, the engagement portion 332 can be more rigid than the flexible tail portion 334. In some embodiments, the flexible tail portion 334 can be about 20% more flexible than the engagement portion 332. In some embodiments, the branch stent 330 can include a transition portion (not shown) disposed between the engagement portion 332 and the flexible tail portion 334 and coupling the engagement portion 332 to the flexible tail portion 334. The engagement portion 332 can include a proximal portion 331, an intermediate portion 335, and a distal portion 333. When the branch stent 330 is in the expanded configuration, a diameter of the intermediate portion 335 can be less than the diameter of the proximal portion 331 and the diameter of the distal portion 333 such that the engagement portion 332 of the branch stent 330 has, for example, a saddle or hourglass shape. In some embodiments, the flexible tail portion 334 can be any suitable diameter in a deployed configuration (e.g., as shown in FIG. 5D) relative to a diameter of the engagement portion 332 (e.g., the diameter of the intermediate portion 335) or a diameter of the coupling portion 320.

In some embodiments, the branch stent 330 or a portion of the branch stent 330 can have a lower radial strength than the radial strength of the coupling member 320. For example, in some embodiments, the radial strength of the target zone or intermediate portion 335 of the engagement portion can be less than the radial strength or resistance to expansion of the coupling member 320. Thus, as the branch stent 330 is expanded, the intermediate portion 335 can be prevented from expanding to as great of a diameter as the proximal portion 331 or the distal portion 333 by the coupling member 320. Similarly, due to the contracting force of the coupling member 320 being greater than the radial force applied by the target zone or intermediate portion 335 of the branch stent 330 against the coupling member 320, the contracting force of the coupling member 320 can be sufficient to compress the target zone after the expanding member 340 has been removed.

In some embodiments, the proximal portion 331 can include a band or ring of closed cells. The band or ring of closed cells can be positioned proximal the fenestration 365. One, some, or all of the closed cells in the band can have a diamond shape. The band or ring of closed cells can be configured and positioned to provide increased radial strength to the proximal end of the branch stent 330 to prevent the branch stent 330 from collapsing (e.g., due to the force applied by the coupling member 320 during expansion of the branch stent 330). For example, in some embodiments, the band or ring can have increased radial strength and be more resilient to compression than a weakened or target portion of the branch stem 330. The band or ring of closed cells can also prevent the expandable member 340 from moving proximally relative to the branch stent 330 (e.g., during the expansion of the expandable member 340).

In some embodiments, the engagement portion 332 can include a target zone configured to interface with the coupling member 320. In some embodiments, the target zone can include the intermediate portion 335. In some embodiments, the target zone can include the intermediate portion 335 and a portion of one or both of the proximal portion 331 and the distal portion 333. The target zone can have any suitable length. For example, the target zone can have a length in the range of about 2 mm to about 12 mm, about 2 mm to about 8 mm, and about 3 mm to about 6 mm. In some embodiments, the intermediate portion 335 or target zone can include a weakened area such that the intermediate portion 335 or target zone can be less resilient to compression in the weakened area. In some embodiments, the target zone can have a plurality of engagement struts (not shown) configured to selectively engage the coupling member 320 when the branch stent 330 (and thus the target zone) is in an expanded state. In other words, the branch stent 330 can be delivered to a treatment site (e.g., via a delivery catheter), the engagement struts can be positioned relative to the coupling member 320, and the plurality of engagement struts can be moved into engagement with the coupling member 320 (e.g., via expanding an expandable member 340). The plurality of engagement struts can form at least a portion of the weakened area of the intermediate portion 335 or target zone. In some embodiments, the plurality of engagement struts can include three to twelve engagement struts. In some embodiments, the plurality of engagement struts can include four to six engagement struts. The engagement struts can define openings or windows in the engagement portion 332 of the branch stent 330, each of the openings or windows being disposed between two engagement struts. Thus, due to the openings or windows between the engagement struts, the engagement struts can be sufficiently thin such that the engagement struts can be less resilient to compression than other portions of the branch stent 330.

In some embodiments, the intermediate portion 335 or target zone can include a weakened portion that is less resilient to compression than other portions of the branch stent 330 due to being less thick, less wide, of a more elastic material, or shaped such that the weakened portion is sufficiently compressible. In some embodiments, some engagement struts of the plurality of engagement struts can be more rigid than others, such that some of the engagement struts are less resilient to compression and/or expansion than other engagement struts. The openings or windows referred to herein can include pass-through, cut-outs, less rigid structures (e.g., struts) disposed between more rigid structures (e.g. more rigid struts), and/or any other suitable weakened area or structure that an expandable member (e.g., expandable member 340)_can expand into or displace relative to other portions of an engagement portion (e.g., engagement portion 332) of a stent. In some embodiments, the openings or windows referred to herein can be covered and an expandable member (e.g., expandable member 340) can expand into the space defined by, for example, the struts and the cover. In some embodiments, the openings or windows referred to herein can be uncovered such that an expandable member (e.g., expandable member 340) can expand into the space defined by, for example, the struts, and can further expand through the openings or windows and beyond the outer surface of the engagement portion (e.g., engagement portion 332).

Figure 10:
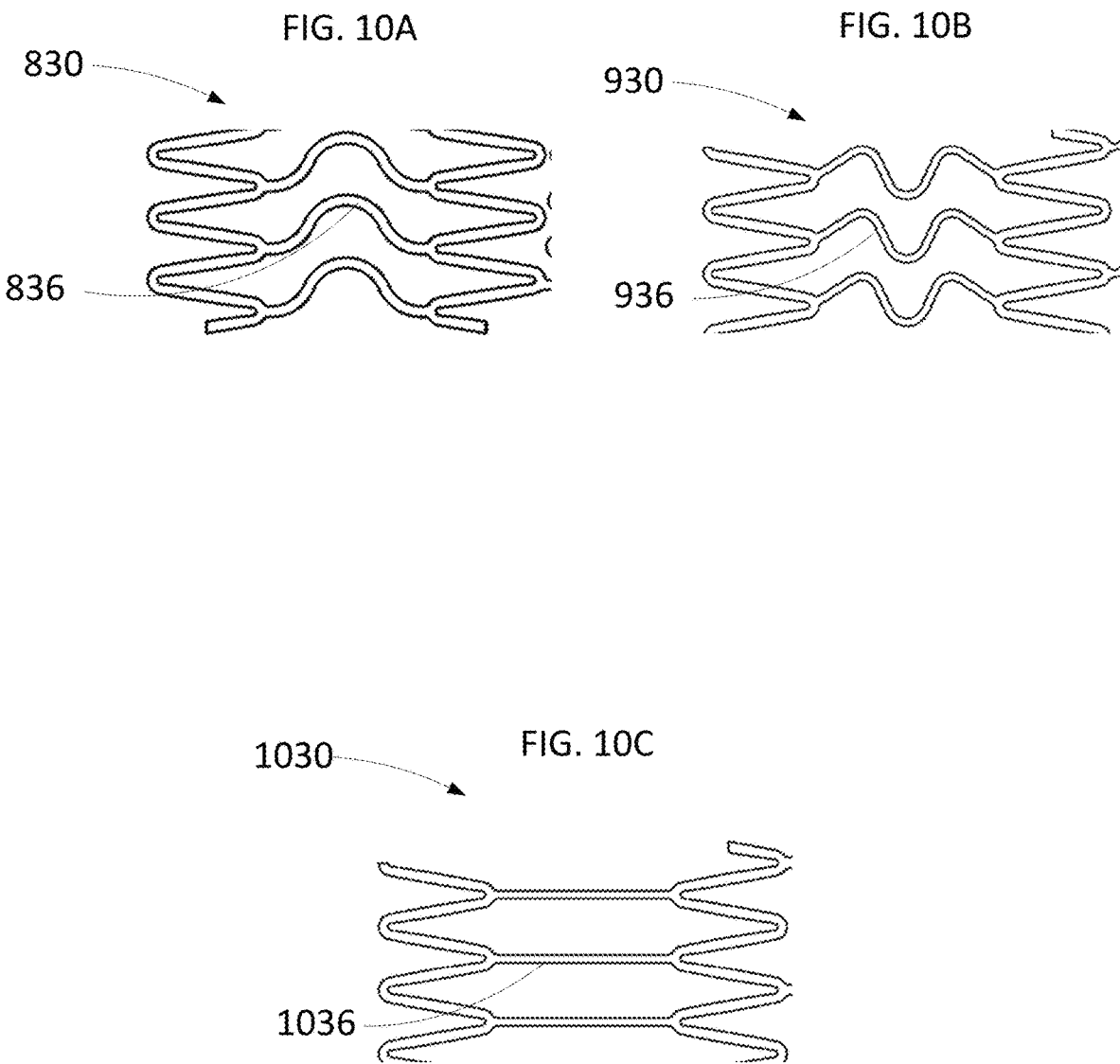
FIG. 10A is an opened and flattened view of a portion of a branch stent, according to an embodiment.
FIG. 10B is an opened and flattened view of a portion of a branch stent, according to an embodiment.
FIG. 10C is an opened and flattened view of a portion of a branch stent, according to an embodiment.

In some embodiments, the plurality of engagement struts can have particular shapes such that, during expansion of the branch stent 330 and/or contraction of the coupling member 320, the coupling member 320 can align with a particular portion of the engagement portion 332 of the branch stent 330. Said another way, the engagement portion 332 can be shaped and/or structured such that the engagement portion 332 can self-align with the coupling member 320 when the branch stent 330 transitions from the contracted configuration to the expanded configuration or when the coupling member 320 transitions from the expanded configuration to the contracted configuration. In some embodiments, the engagement portion 332 can self-align with the coupling member 320 due to the engagement struts having a weakened portion, a curved portion, a flexible portion, or some other type of structure or shape that causes the engagement struts or a particular segment of the engagement struts to be more susceptible to being contracted or contracted to a smaller diameter by the coupling member 320 than another portion of the branch stent 330 or another segment of the engagement struts. Some example engagement strut shapes are shown and described below with respect to branch stents 830, 930, 1030, and 1130 as shown in FIGS. 10A-10C, respectively.

In some embodiments, the engagement portion 332 can include a protruding tab (not shown) configured to selectively engage the coupling member 320. In other words, the protruding tab can be disposed near the coupling member 320 and moved into engagement with the coupling member 320 via, for example, the expandable member 340. In some embodiments, the engagement portion 332 can include a first protruding tab (not shown) configured to be disposed proximal to the coupling member 320 and/or a second protruding tab (not shown) configured to be disposed distal to the coupling member 320. The first protruding tab and the second protruding tab can be configured to engage the coupling member 320.

In some embodiments, the engagement portion 332 can include a first set of protruding tabs (not shown) configured to be disposed proximal to the coupling member 320 and/or a second set of protruding tabs (not shown) configured to be disposed distal to the coupling member 320. The first set of protruding tabs and the second set of protruding tabs can be configured to engage the coupling member 320. For example, each of the protruding tabs in the first set of protruding tabs can be configured to be aligned with a corresponding protruding tab in the second set of protruding tabs. Each of the protruding tabs in the first set of protruding tabs can be configured to be offset from a corresponding protruding tab in the second set of protruding tabs. The first set of protruding tabs and the second set of protruding tabs can each include at least two protruding tabs, at least three protruding tabs, at least four protruding tabs, at least five protruding tabs, at least six protruding tabs, at least seven protruding tabs, at least eight protruding tabs, at least nine protruding tabs, at least ten protruding tabs, at least eleven protruding tabs, at least twelve protruding tabs, between two and twelve protruding tabs, between three and eight protruding tabs, between four and six protruding tabs, or any suitable number of protruding tabs. In some embodiments, each protruding tab of the engagement portion 332 can have an undeployed state and a deployed state. In the deployed state, each protruding tab of the engagement portion 332 can protrude beyond the outer surface of the branch stent 330 by a distance equal to at least about 20% of the nominal thickness of the frame of the branch stent 330.

The expandable member 340 can be or include, for example, a balloon. The expandable member 340 can be expandable via any suitable fluid, such as, for example, air or a liquid. The expandable member 340 can include a first portion 342 and a second portion 344. The first portion 342 of the expandable member 340 can be configured to expand the engagement portion 332 of the branch stent 330. The second portion 344 of the expandable member 340 can be configured to expand the flexible tail portion 334 of the branch stent 330. In some embodiments, when the expandable member 340 is in the expanded configuration, the first portion 342 of the expandable member 340 can have a larger diameter than the second portion 344 of the expandable member 340. In some embodiments, the expandable member 340 can have a stepped outer profile such that the first portion 342 has a first constant diameter and the second portion 344 has a second constant diameter, the first portion 342 and the second portion 344 being coupled by a tapered transition portion. In some embodiments, rather than the expandable member 340 having a stepped outer profile, the first portion 342 can have a saddle or hourglass shaped outer profile. In other words, the first portion 342 of the expandable member can include a proximal portion 341, an intermediate portion 345, and a distal portion 343. When in the expanded configuration, the intermediate portion 345 can have a diameter less than the diameter of the proximal portion 341 and/or the distal portion 343.

In some embodiments, the expandable member 340 can be formed of a semi-compliant material. In some embodiments, the first portion 342 of the expandable member 340 can be formed of a semi-compliant material and the second portion 344 of the expandable member 340 can be formed of a non-compliant material. In some embodiments, the first portion 342 of the expandable member 340 can have a first compliance and the second portion 344 of the expandable member 340 can have a second compliance less than the first compliance. In some embodiments, the expandable member 340 (e.g., both the first portion 342 and the second portion 344) has a compliance of less than about 10%. The compliance of the expandable member 340 can be determined using the following equation.

$$\text{Compliance (\%)} = \frac{(\emptyset_{High\ ATM} - \emptyset_{Low\ ATM})}{\emptyset_{Low\ ATM}} \times 100\%$$

In some embodiments, the expandable member 340 is initially extruded as a balloon with a constant wall thickness and a substantially constant diameter. The first portion 342 can be formed such that the first portion 342 has a reduced wall thickness compared to the second portion 342. When the expandable member 340 is inflated, the first portion 342 having reduced wall thickness will expand before and/or more quickly than the second portion 344. The first portion 342 can expand such that the first portion 342 engages with engagement struts of the engagement portion 332 of the branch stent 330. As the first portion 342 continues to expand, the first portion 342 can expand into a weakened area (e.g., the openings or windows) in the engagement portion 332 of the branch stent 330, securing the expandable member 340 relative to the branch stent 330. Thus, the branch stent 330 can be prevented from separating from the expandable member 340 during the expansion of the expandable member 340.

In some embodiments, a portion of the first portion 342 can expand into the weakened area (e.g., openings or windows) in the engagement portion 332 before the engagement portion 332 begins to expand under the expanding force of the expandable member 340. In some embodiments, a portion of the first portion 342 distal of a proximal end portion of the expandable member 340 can expand to an increased outer diameter compared to the outer diameter of the proximal end portion of the expandable member 340 prior to the expansion of, for example, a band or ring of closed cells in the proximal portion 331 of the branch stent 330. In some embodiments, prior to or at the point of the engagement portion 332 of the branch stent 330 first expanding into a contact relationship with the coupling member 320, the expandable member 340 and the branch stent 330 can have a larger diameter in, for example, the intermediate portions 345 and 335 of the expandable member 340 and the branch stent 330, respectively, or the target zone of the branch stent 330 than the diameter of the proximal portions 341 and 331 of the expandable member 340 and the branch stent 330, respectively and/or distal portions 343 and 333 of the expandable member 340 and the branch stent 330, respectively.

In some embodiments, the first portion 342 and the second portion 344 of the expandable member 340 can be in fluidic communication with each other and fluidically coupled to a single fluid supply mechanism, such as a tube. In some embodiments, the expandable member 340 can include a radiopaque marker or band (not shown). The radiopaque marker or band can be positioned near or within the intermediate portion 345 of the first portion 342 of the expandable member 340 such that, when the branch stent 330 is aligned with the expandable member 340 such that the intermediate portion 335 of the branch stent 330 is aligned with the intermediate portion 345 of the expandable member 340, the target zone of the branch stent 330 can be aligned with the coupling member 320 using, for example, radiographic imaging.

In some embodiments, the branch stent 330 can include a stent cover (not shown). In some embodiments, the stent cover can full cover the entire outer surface of the branch stent 330. In some embodiments, the stent cover can cover only the tail portion 334 of the branch stent 330. In some embodiments, the stent cover can cover the tail portion 334 and at least a portion of a transition portion and/or engagement portion 332 of the branch stent 330. The stent cover can be formed of any suitable material, such as, for example, expanded polytetrafluoroethylene (ePTFE) or espun poly (tetrafluoroethylene) (espun PTFE). The cover can have the same or similar strain potential as described in International Application No. PCT/US2017/044822, filed Aug. 1, 2017, entitled "Systems, Devices, and Methods for Coupling a Prosthetic Implant to a Fenestrated Body", Which is hereby incorporated by reference in its entirety.

For example, as shown in FIG. 5A, the expandable member 340 can be disposed within a lumen of the branch stent 330. The branch stent 330 and the expandable member 340 can then be inserted into the fenestration 365 of the fenestrated body 360 such that the coupling member 320 surrounds the branch stent 330 and the expandable member 340. More specifically, the branch stent 330 and the expandable member 340 can be disposed within the fenestration 365 such that a target zone (e.g., the intermediate portion 335) of the branch stent 330 is aligned with the coupling member 320.

As shown in FIG. 5B, the expandable member 340 can then be expanded (e.g., inflated) such that the expandable member 340 applies an expanding force against the inner wall of the branch stent 330. The expanding force can cause the branch stent 330 to expand in diameter and engage with the coupling member 320. The expandable member 340 can be further expanded such that the expanding force of the expandable member 340 causes the branch stent 330 to apply an expanding force to the coupling member 320 such that the coupling member 320 expands from a first diameter D1 (shown in FIG. 5A) to a second diameter D2 (shown in FIG. 5B). In some embodiments, the second diameter D2 can be up to three times the first diameter D1. In some embodiments, the expansion of the expandable member 340 can cause the proximal portion 331 and the distal portion 333 of the branch stent 330 to further expand on the proximal side and the distal side, respectively, of the coupling member 320. The lack of resistance (compared to the resistance to the expanding force of the expandable member 340 in combination with the branch stent 330 applied by the coupling member 320) allows the branch stent 330 to expand to a saddle-like shape with the proximal portion 341 on the proximal side of the coupling member 320 and the distal portion 343 on the distal side of the coupling member 320. In other words, each of the proximal portion 341 and the distal portion 343 can have a larger diameter than the diameter of the coupling member 320 and the intermediate portion 345 of the expandable member 340 in the configuration shown in FIG. 5B.

Figure 5C:
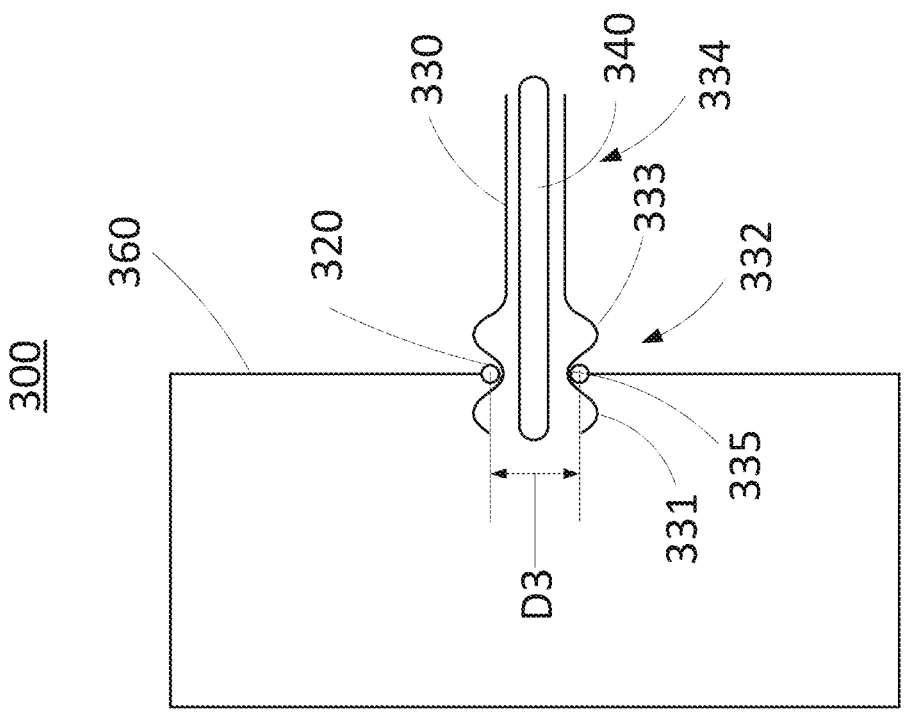

As shown in FIG. 5C, the expandable member 340 can then be contracted (e.g., deflated) such that the expanding force previously applied by the expandable member 340 against the branch stent 330 and the coupling member 320 is removed. As a result, the coupling member 320 can contract to a third configuration with a third diameter D3. In some embodiments, the branch stent 330 (including the proximal portion 331, the intermediate portion 335, and the distal portion 333 can contract due to the removal of the expanding force applied by the expandable member 340. In some embodiments, the branch stent 330 can contract due to a contraction force applied by the coupling member 320 to the intermediate portion 335 when the coupling member 320 contracts to the third configuration. In some embodiments, the third diameter D3 can be greater than the first diameter D1. In some embodiments, the third diameter D3 can be substantially equal to the first diameter D1.

As shown in FIG. 5D, the expandable member 340 can be removed from within the branch stent 330, leaving the branch stent 330 secured to the fenestrated body 360 via the coupling member 320. In such a configuration, the coupling member 320 and the branch stent 330 can be coupled such that the branch stent 330 can pivot about the fenestration 365 of the fenestrated body 360 and the axial movement of the branch stent 330 relative to the fenestrated body 360 is limited due to the contraction force applied by the coupling member 320 on the intermediate portion 335 of the branch stent 330.

In some embodiments, the first portion 342 of the expandable member 340 can be configured to have a diameter in the expanded configuration that is greater than an inside diameter of the coupling member 320 after the expandable member 340 has been expanded and contracted (see FIG. 5C). In some embodiments, the diameter of the expandable member 340 (and thus, the proximal portion 331 and the distal portion 333 of the branch stent 330) in the expanded state (see FIG. 5B) can be at least about 0.5 mm greater than the inside diameter of the coupling member 320 in the third configuration (see FIG. 5C).

Figure 6:
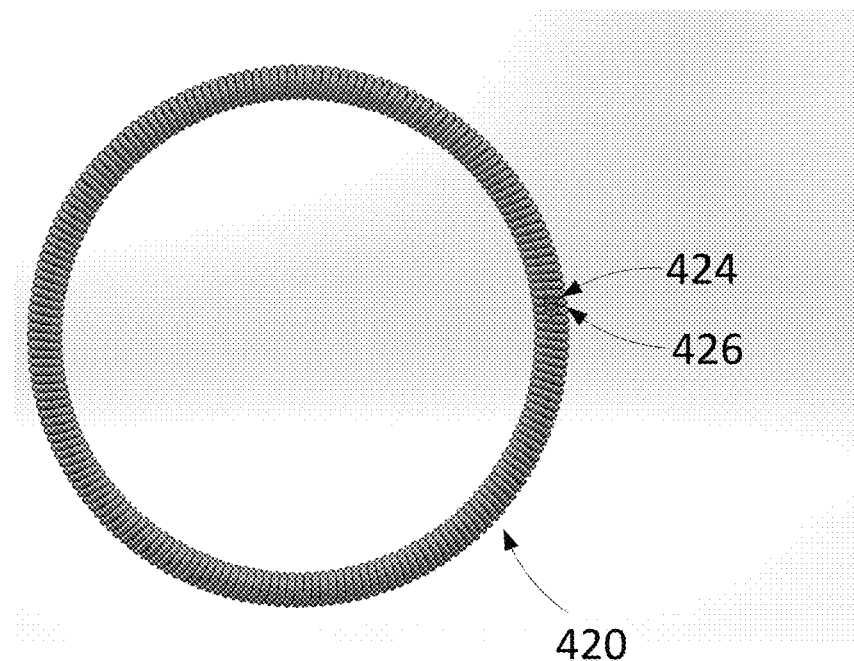
FIG. 6 is a front view of a coupling member, according to an embodiment.

FIG. 6 is a front view of a radially expandable coupling member 420. The coupling member 420 can be the same or similar in structure and/or function to any of the coupling members described herein. For example, the coupling member 420 can be formed as a coil having a first end 424 and a second end 426. The first end 424 can be coupled to the second end 426 via any suitable connection method or mechanism (e.g., via welding) such that the coupling member 420 forms a ring. The coupling member 420 can be coupled to a fenestrated body (e.g., the fenestrated body 360) such that the coupling member 420 is disposed about (e.g., fully or completely surrounding) a fenestration defined by the fenestrated body (e.g., the fenestration 365).

The coupling member 420 can be coupled to a fenestrated body via any suitable coupling mechanism. For example, the coupling member 420 can be stitched to a fenestrated body using, for example, sutures. In some embodiments, the coupling member 420 can be coupled to a fenestrated body via polyurethane. In some embodiments, the coupling member 420 can be coupled to a fenestrated body via a mechanical coupling, via welding, or via any apparatus or method described in the '157 application.

The coupling member 420 can be configured to expand from a first configuration having a first diameter to a second configuration having a second diameter in response to the application of an expanding force, such as an expanding force applied by any of the expandable members described herein (e.g., expandable member 340). After expanding, the coupling member 420 can be configured to contract from the second configuration to a third configuration having a third diameter upon removal of the expanding force. In some embodiments, the third diameter can be substantially equal to the first diameter. In some embodiments, the third diameter can be greater than the first diameter. Additionally, the coupling member 420 can be configured to engage with a branch stent graft, such as any of the branch stents described herein (e.g., branch stent 330). For example, an expandable member can be expanded within a branch stent such that the expandable member applies an expanding force to an inner wall of the branch stent, causing an outer wall of the branch stent to contact, engage with, and/or expand the coupling member 420 from the first configuration to the second configuration. When the expanding force is removed (e.g., via deflation and/or removal of the expandable member), the coupling member 420 can contract and apply a force to the branch stent sufficient to decrease a diameter of the branch stent.

Figure 7:
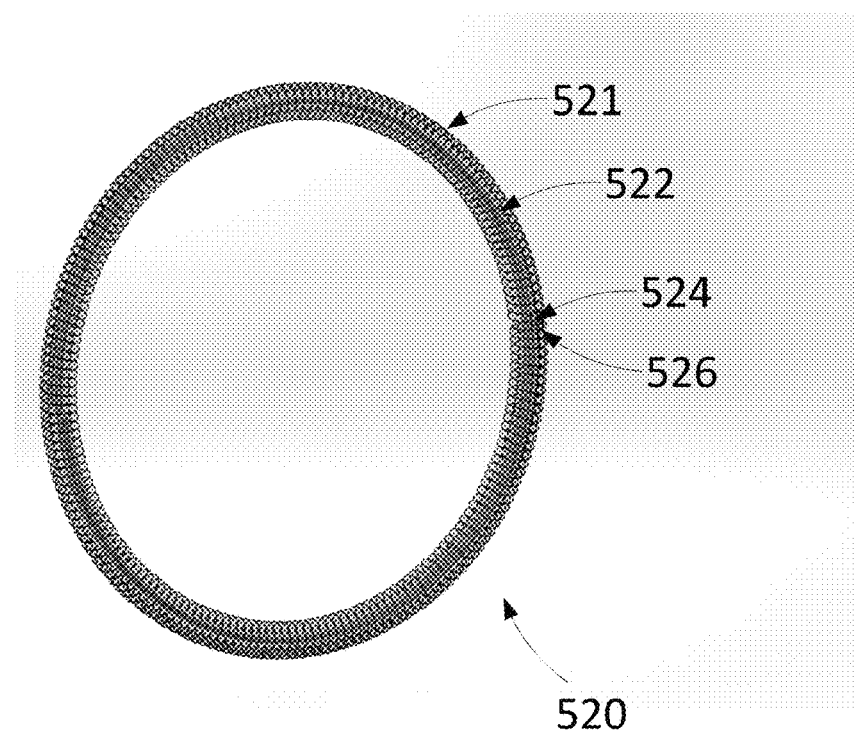
FIG. 7 is a front view of a coupling member, according to an embodiment.

FIG. 7 is a perspective view of a radially expandable coupling member 520. The coupling member 520 can be the same or similar in structure and/or function to any of the coupling members described herein. For example, the coupling member 520 can include a coil 521 having a first end 524 and a second end 526. The first end 524 can be coupled to the second end 526 via any suitable connection method or mechanism e.g., via welding) such that the coupling member 520 forms a ring. The coupling member 520 can be coupled to a fenestrated body (e.g., the fenestrated body 360) such that the coupling member 520 is disposed about (e.g., fully or completely surrounding) a fenestration defined by the fenestrated body (e.g., the fenestration 365).

The coupling member 520 can include a shape memory core 522 disposed within the coil 521 (e.g., within a central lumen of the coil 521). The shape memory core 522 can include a shape memory material or structure such that the shape memory core 522 can revert to a predetermined shape (e.g., a circular shape). For example, the shape memory core 522 can include a shape memory material such that the coupling member 520 can revert to a circular shape after being collapsed or compressed for delivery to a particular vascular location via a delivery sheath. The shape memory core 522 can also prevent kinking of the coil during the collapsing, delivery, and expansion of the coil at the desired vascular location. In some embodiments, the shape memory core 522 can include a shape memory alloy, such as, for example, Nitinol (i.e., nickel titanium). In some embodiments, the coil 521 in combination with the shape memory core 522 can have a spring rate of at least about 0.025 N/mm. In some embodiments, the coil 521 alone (i.e., without the shape memory core 522) can have a spring rate of at least about 0.025 N/mm.

Figure 8A:
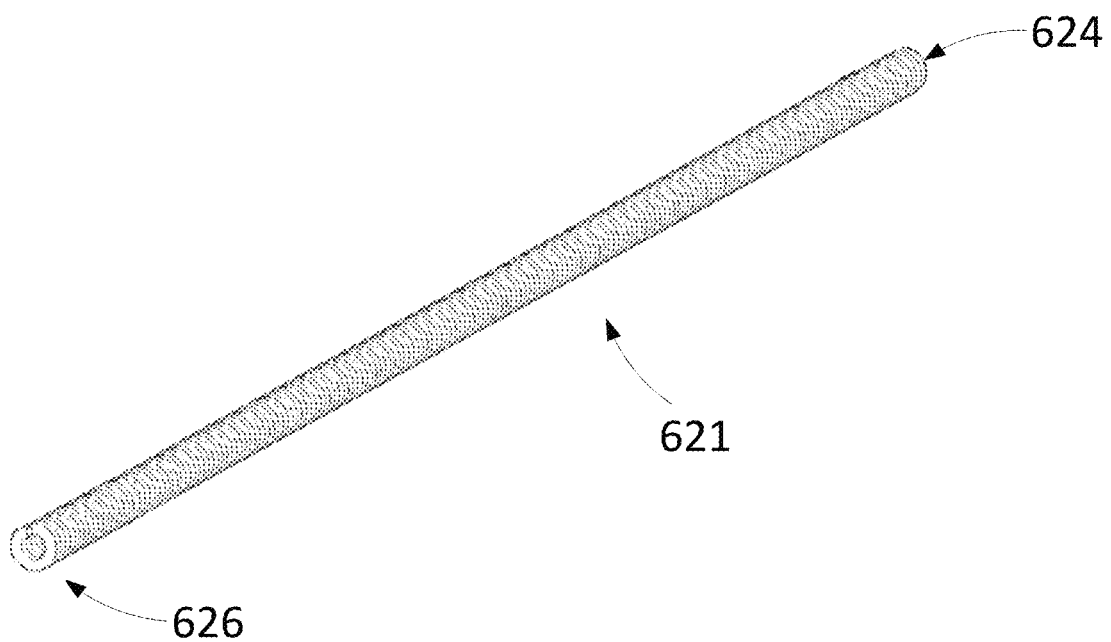
FIG. 8A is a perspective view of a coil, according to an embodiment.
Figure 8B:
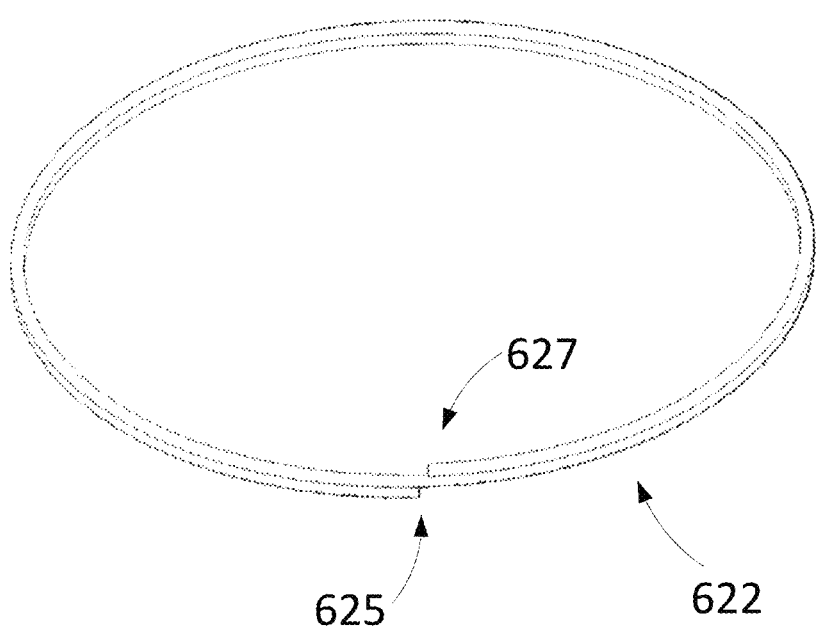
FIG. 8B is a perspective view of a shape memory core, according to an embodiment.

FIGS. 8A and 8B are a perspective view of a coil 621 and a shape memory core 622 of a radially expandable coupling member in an unassembled configuration, respectively. The coil 621 and the shape memory core 622 can be the same or similar in structure and/or function to any of the coils or shape memory cores, respectively, described herein. For example, the coil 621 has a first end 624 and a second end 626. The first end 624 can be coupled to the second end 626 via any suitable connection method or mechanism (e.g., via welding) such that the coil 621 forms a ring. The coil 621 can be coupled to a fenestrated body (e.g., the fenestrated body 360) such that the coil 621 is disposed about (e.g., fully or completely surrounding) a fenestration defined by the fenestrated body (e.g., the fenestration 365).

As shown in FIG. 8B, the shape memory core 622 can be shaped as a split key ring having a first end 625 and a second end 627. The shape memory core 622 can be coupled to and/or disposed within a coupling member such as the coil 621 of FIG. 8A. For example, the coil 621 can be threaded over the shape memory core 622 (e.g., the first end 625 can be threaded through a central lumen of the coil 621) until the shape memory core 622 is fully within the coil 621 and the first end 624 and the second end 626 of the coil have been coupled together. Due to the split key ring shape of the shape memory core 622, when the coil 621 expands, the shape memory core 622 can also expand and the first end 625 of the shape memory core 622 can separate from the second end 627 of the shape memory core 622. When the coil 621 contracts to a smaller diameter, the shape memory core 622 can also contract and the first end 625 of the shape memory core 622 can move closer to the second end 627 of the shape memory core 622.

Figure 9:
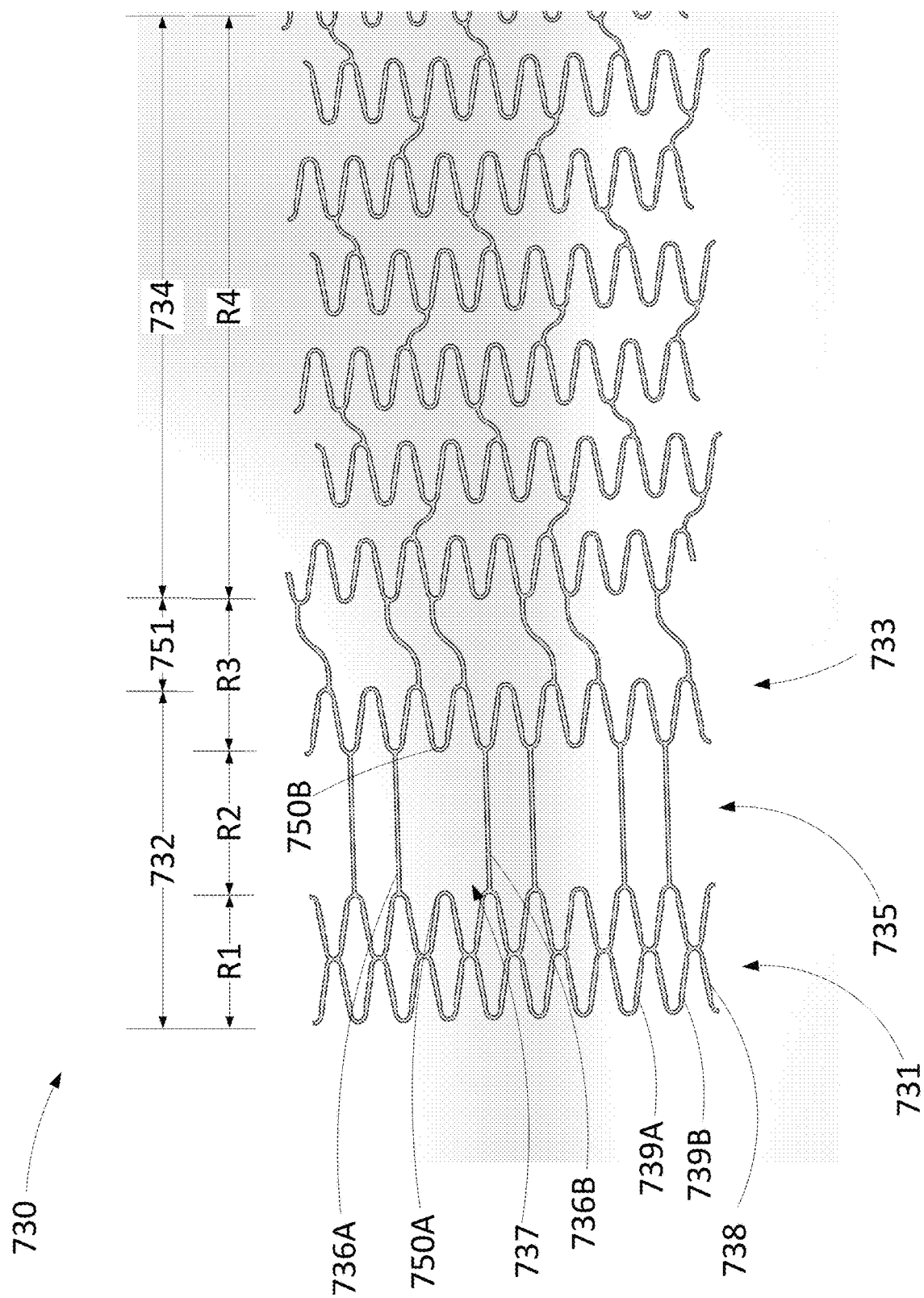
FIG. 9 is an opened and flattened view of a portion of a branch stent, according to an embodiment.

FIG. 9 is a top view of a portion of a branch stent 730 in an undeformed, initial state, but cut and unrolled into a flat sheet for ease of illustration. The branch stent 730 can be the same or similar in structure and/or function to any of the branch stents described herein, such as branch stent 330. As shown in FIG. 9, the branch stent 730 includes an engagement portion 732, a transition portion 751, and a flexible tail portion 734. The engagement portion 732 can include a proximal portion 731, an intermediate portion 735, and a distal portion 733. Said another way, the branch stent 730 can have four regions: a first region R1, a second region R2, a third region R3, and a fourth region R4. The first region R1 can include the proximal portion 731 of the branch stent 730, the second region R2 can include the intermediate portion 735 of the branch stent 730, the third region R3 can include the distal region 733 and the transition portion 751 of the branch stent 730, and the fourth region R4 can include the flexible tail portion 734 of the branch stent.

The proximal portion 731 (i.e., the first region R1) of the branch stent 730 can include a band or ring 738. The band 738 can include a number of closed cells, such as, for example, closed cell 739A and closed cell 739B. Each of the closed cells 739 can have a diamond shape. The band 738 can be configured and positioned relative to an expanding member (e.g., a balloon) or coupling member such that the band 738 can provide increased radial strength to the proximal end of the branch stent 330 from collapsing or shifting relative to the expanding member or the coupling member.

As shown in FIG. 9, the intermediate portion 735 (i.e., the second region R2) of the branch stent 730 can include a number of engagement struts 736, such as, for example, engagement strut 736A and engagement strut 736B. The engagement struts can be configured to selectively engage a coupling member (such as coupling member 320) when the branch stent 730 is in an expanded state. Although the branch stent 730 is shown as including six engagement struts 736, the branch stent 730 can include any suitable number of engagement struts.

The engagement struts 736 can partially defined windows or openings 737 between the engagement struts 736 that can form a weakened area of the branch stent 730. For example, engagement strut 736A and engagement strut 736B can form opposite sides of an opening 737. The openings 737 can be shaped and/or sized such that an expandable member (e.g., a balloon) can expand into engagement with the engagement struts 736 and can further expand into the opening 737 such that the expandable member is secured or anchored to the branch stent 730. In some embodiments, the engagement struts 736 can be disposed in pairs such each pair is spaced from another pair by a closed cell from the band 738, creating wider openings 737 between pairs of engagement struts 736.

Additionally, in some embodiments, the engagement portion 732 can include protruding tabs 750 (also referred to as "locking tabs"). The protruding tabs 750 can be configured to selectively engage a coupling member the coupling member 320). For example, the engagement portion 732 includes a first protruding tab 750A configured to be disposed proximal to a coupling member and a second protruding tab 750B configured to be disposed distal to the coupling member. The first protruding tab 750A and the second protruding tab 750B can be configured to selectively engage a coupling member. The first protruding tab 750A can be configured to align with the second protruding tab 750B on opposite sides of a coupling member. As shown in FIG. 9, a pair of protruding tabs 750 can be disposed between pairs of engagement struts 736. In some embodiments, each protruding tab 750 can have an undeployed state and a deployed state. In the deployed state, each protruding tab 750 can protrude beyond the outer surface of the branch stent 730 by a distance equal to at least about 20% of the nominal thickness of the frame of the branch stent 730. In some embodiments, as shown in FIG. 9, a protruding tab 750 can form a portion of a closed cell 739 of the band 738.

FIGS. 10A-10C are views of various engagement strut shapes in unexpanded configurations. Specifically, FIG. 10A shows a portion of a branch stent 830. The branch stent 830 includes engagement struts 836. The engagement struts 836 have a curved or semi-circular shape.

FIG. 10B shows a portion of a branch stent 930. The branch stent 930 includes engagement struts 936. The engagement struts 936 can have a sinusoidal shape, serpentine shape, or a shape including three or more curves.

FIG. 10C shows a portion of a branch stent 1030. The branch stent 1030 includes engagement struts 1036. The engagement struts 1036 have a straight shape.

Figure 11:
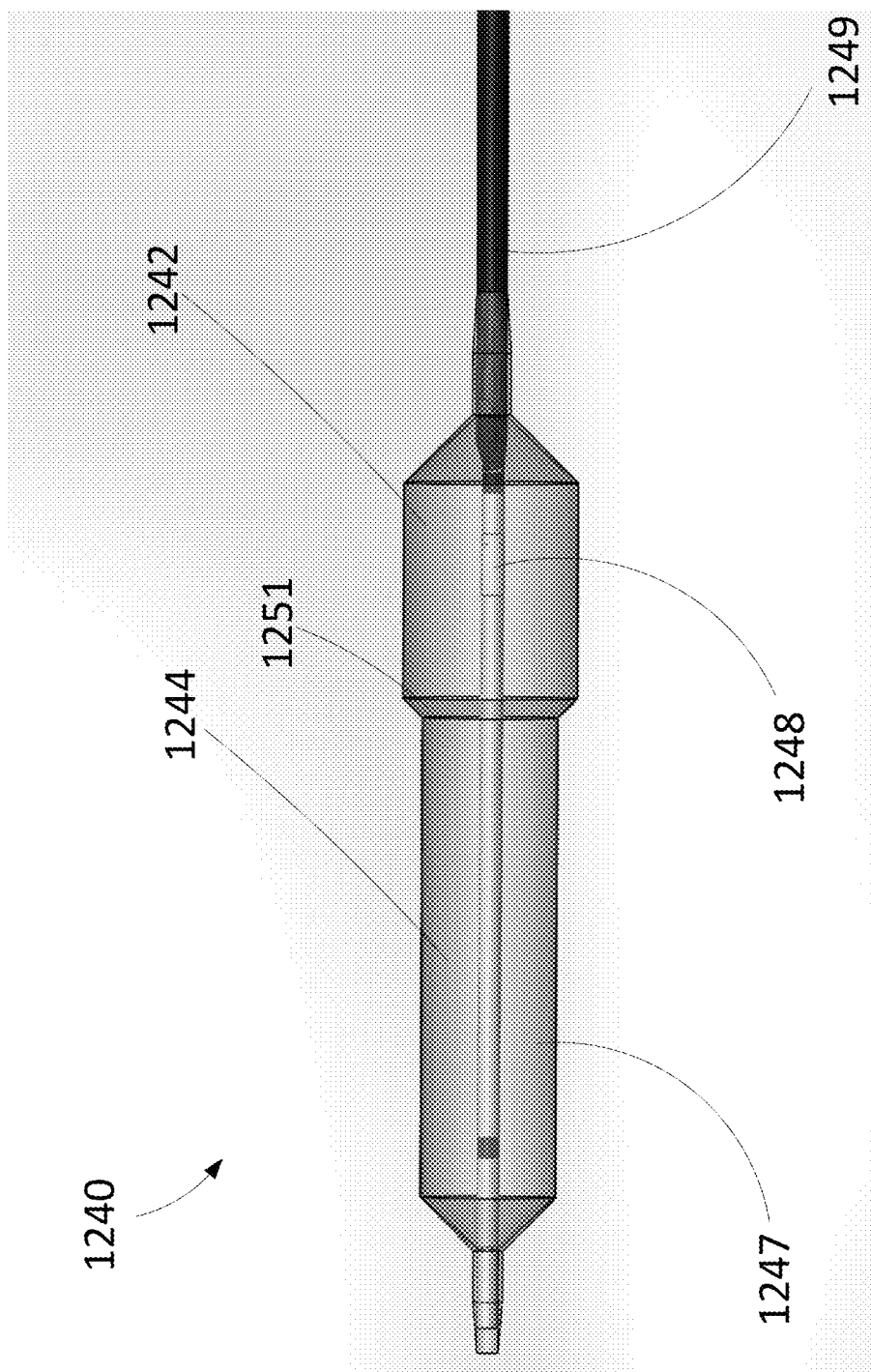
FIG. 11 is a side view of an expandable member in an expanded configuration, according to an embodiment.

FIG. 11 is a side view of an expandable member 1240 in an expanded configuration. The expandable member 1240 can be the same or similar in structure and/or function to any of the expandable members described herein, such as, for example, the expandable member 340. The expandable member 1240 can include a balloon 1247. The balloon 1247 can include a first portion 1242 and a second portion 1244. As shown in FIG. 11, expandable member 1240 can have a stepped outer profile such that the first portion 1242 and the second portion 1244 each have a substantially constant outer diameter, the first portion 1242 and the second portion 1244 being coupled by a tapered transition portion 1251.

The expandable member 1240 can also include an inflation tube 1249. The inflation tube 1249 can be partially disposed within the balloon 1247 and can be coupled to a source of inflation fluid outside of the balloon 1247 such that the balloon 1247 can be fluidically coupled to the source of inflation fluid. The inflation tube 1249 can be configured to inflate both the first portion 1242 and the second portion 1244 via delivery of inflation fluid to one or both of the first portion 1242 and the second portion 1244.

The first portion 1242 of the expandable member 1240 can be configured to expand an engagement portion of a branch stent (e.g., the branch stent 330). The second portion 1244 of the expandable member 1240 can be configured to expand a flexible tail portion of a branch stent. As shown, when the expandable member 1240 is in the expanded configuration, the first portion 1242 of the expandable member 1240 can have a larger diameter than the second portion 1244 of the expandable member 1240.

In some embodiments, balloon 1247 of the expandable member 1240 can be initially formed as a balloon with a two wall thicknesses. The first portion 1242 can be stretched such that the first portion 1242 has a reduced wall thickness compared to the second portion 1242. When the balloon 1247 is inflated, the first portion 1242 having reduced wall thickness will expand before and more quickly than the second portion 1244. The first portion 1242 can expand such that the first portion 1242 engages with engagement struts of an engagement portion of a branch stent (e.g., the branch stent 330). As the first portion 1242 continues to expand, the first portion 1242 can expand into openings or windows in the engagement portion of the branch stent, securing the expandable member 1240 relative to the branch stent. Thus, the branch stent can be prevented from separating from the expandable member 1240 during the expansion of the expandable member 1240.

In some embodiments, the expandable member 1240 can include a radiopaque marker or band 1248. The radiopaque marker or band 1248 can be positioned within the first portion 1242 of the expandable member 1240 such that, when a branch stent is aligned with the expandable member 1240 such that an engagement portion of the branch stent is aligned with the first portion 1242 of the expandable member 1240, a target zone of the branch stent can be aligned with a coupling member (such as, for example coupling member 320) using, for example, radiographic imaging.

Figure 12:
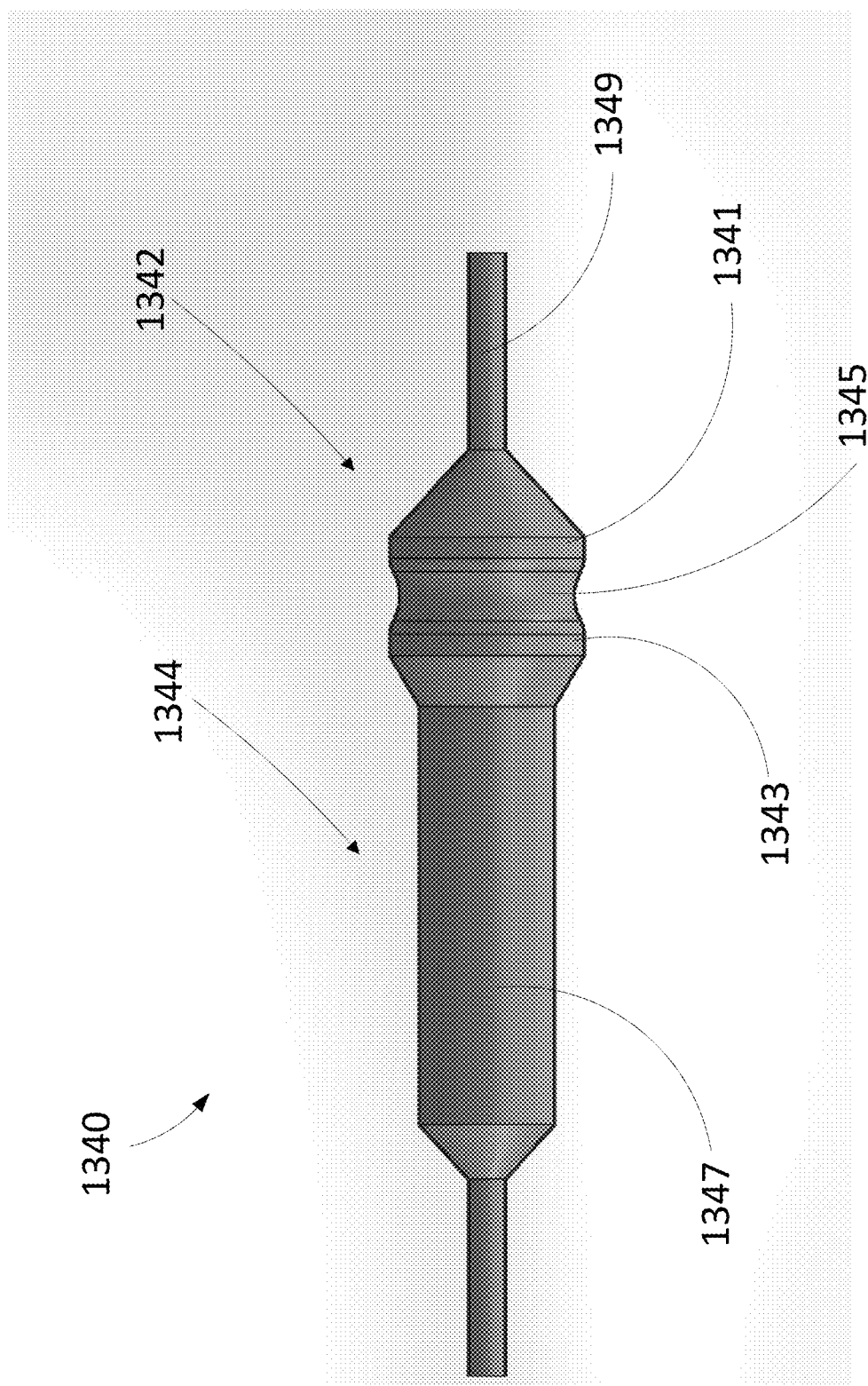
FIG. 12 is a side view of an expandable member in an expanded configuration, according to an embodiment.

FIG. 12 is a side view of an expandable member 1340 in an expanded configuration. The expandable member 1340 can be the same or similar in structure and/or function to any of the expandable members described herein, such as, for example, the expandable member 340. The expandable member 1340 can include a balloon 1347. The balloon 1347 can include a first portion 1342 and a second portion 1344. As shown in FIG. 11, the first portion 1342 can have a saddle or hourglass shaped outer profile. In other words, the first portion 1342 of the expandable member can include a proximal portion 1341, an intermediate portion 1345, and a distal portion 1343. When in the expanded configuration, the intermediate portion 1345 can have a diameter less than the diameter of the proximal portion 1341 and/or the distal portion 1343.

The expandable member 1340 can also include an inflation tube 1349. The inflation tube 1349 can be partially disposed within the balloon 1347 and can be coupled to a source of inflation fluid outside of the balloon 1347 such that the balloon 1347 can be fluidically coupled to the source of inflation fluid. The inflation tube 1349 can be configured to inflate both the first portion 1342 and the second portion 1344 via delivery of inflation fluid to one or both of the first portion 1342 and the second portion 1344.

The first portion 1342 of the expandable member 1340 can be configured to expand an engagement portion of a branch stent (e.g., the branch stent 330). The second portion 1344 of the expandable member 1340 can be configured to expand a flexible tail portion of a branch stent. As shown, when the expandable member 1340 is in the expanded configuration, the first portion 1342 of the expandable member 1340 can have a larger diameter than the second portion 1344 of the expandable member 1340.

FIG. 13 is a flow chart showing a method 1400 of deploying a branch stent using any of the assemblies or devices described herein. At 1402, a branch stent can be disposed within a fenestration of a tubular graft such that an engagement portion of the branch stent is aligned with a coupling member disposed about the fenestration. The coupling member can be expandable from a first configuration to a second configuration. At 1404, the branch stent can be radially expanded via an expandable member disposed within the branch stent such that the engagement portion of the branch stent applies an expanding force to the coupling member. The expanding force can be operable to expand the coupling member from the first configuration to the second configuration. At 1406, the expanding force can be removed and the coupling member can be allowed to contract to a third configuration. The coupling member can be operable to apply a contracting force to the branch stent as the branch stent transitions from the second configuration to the third configuration.

While various embodiments of the system, methods and devices have been described above, it should be understood that they have been presented by way of example only, and not limitation. For example, the system, methods, and/or devices described herein can be used with respect to any suitable branch vessel, such as, for example, a juxta-renal, a supra-renal, a para-renal, a thoracic, an iliac, or any other branch vessel. Where methods and steps described above indicate certain events occurring in certain order, those of ordinary skill in the art having the benefit of this disclosure would recognize that the ordering of certain steps may be modified and such modifications are in accordance with the variations of the invention. Additionally, certain of the steps may be performed concurrently in a parallel process when possible, as well as performed sequentially as described above. The embodiments have been particularly shown and described, but it will be understood that various changes in form and details may be made.

For example, although various embodiments have been described as having particular features and/or combinations of components, other embodiments are possible having any combination or sub-combination of any features and/or components from any of the embodiments described herein. In addition, the specific configurations of the various components can also be varied. For example, the size and specific shape of the various components can be different than the embodiments shown, while still providing the functions as described herein.

The invention claimed is:

1. A patient-specific prosthesis for implantation at a treatment site in a patient, the prosthesis comprising:
 a) tubular graft;
 b) a fenestration disposed in the tubular graft, the fenestration corresponding to a predicted branch blood vessel location;
 c) a coupling member disposed about the fenestration, the coupling member including a coil configured to (a) expand from a first configuration to a second configuration in response to the application of an expanding force, and (b) contract to a third configuration upon removal of the expanding force; and
 d) a shape memory core disposed in the coil.

2. The patient-specific prosthesis of claim 1, wherein the coil includes a radiopaque material.

3. The patient-specific prosthesis of claim 2, wherein the radiopaque material includes at least one of tungsten, platinum, gold, and tantalum.

4. The patient-specific prosthesis of claim 1, wherein the coil has a first diameter in the first configuration, a second diameter in the second configuration, and a third diameter in the third configuration.

5. The patient-specific prosthesis of claim 4, wherein the second diameter is up to three times the first diameter.

6. The patient-specific prosthesis of claim 4, wherein the third diameter is greater than the first diameter.

7. The patient-specific prosthesis of claim 4, wherein the third diameter is substantially equal to the first diameter.

8. The patient-specific prosthesis of claim 1, wherein the coil has a spring rate of at least about 0.025 N/mm.

9. The patient-specific prosthesis of claim 1, wherein the coil has a first end and a second end, and the first end is coupled to the second end to form a ring.

10. A patient-specific prosthesis for implantation at a treatment site in a patient, the prosthesis comprising:
 a) a tubular graft;
 b) a fenestration disposed in the tubular graft, the fenestration corresponding to a predicted branch blood vessel location;

c) a coupling member disposed about the fenestration, the coupling member including a coil configured to (a) expand from a first configuration to a second configuration in response to the application of an expanding force, and (b) contract to a third configuration upon removal of the expanding force;

d) a shape memory core disposed in the coil; and e) a branch stent configured to be coupled to the fenestration, the branch stent including an engagement portion for engaging with the coupling member, and a flexible tail portion extending from the engagement portion.

11. A system for treating aneurysms, comprising:

a) a tubular graft;

b) a fenestration disposed in the tubular graft, the fenestration corresponding to a predicted branch blood vessel location;

c) a coupling member disposed about the fenestration, the coupling member configured to expand from a first configuration to a second configuration in response to the application of an expanding force, and contract to a third configuration upon removal of the expanding force;

d) a shape memory core disposed in the coupling member;

e) a radially expandable branch stent configured to be coupled to the fenestration, the branch stent including an engagement portion for engaging with the coupling member, and a flexible tail portion extending from the engagement portion; and f) an expandable member configured to transition the radially expandable branch stent from a collapsed configuration to an expanded configuration, the expandable member having a first portion configured to expand the engagement portion of the branch stent, and a second portion configured to expand the flexible tail portion of the branch stent, the first portion configured to have a diameter in an expanded state greater than an inside diameter of the coupling member in the third configuration.

12. The system of claim 11, wherein:

i) the first portion of the expandable member has a first wall thickness and the second portion of the expandable member has a second wall thickness, the first wall thickness being less than the second wall thickness;

ii) the first portion being in fluid communication with the second portion such that an inflation medium provided to at least one of the first portion and the second portion causes both the first portion and the second portion to inflate, wherein the first portion is inflatable to a larger diameter than the second portion; and iii) the first portion configured such that, when the first portion is engaged with the radially expandable branch stent, an intermediate portion of the first portion can expand into the fenestration defined by the tubular graft such that the expandable member is axially secured relative to the tubular graft.

13. A method, comprising:

a) disposing a branch stent within a fenestration of a tubular graft such that an engagement portion of the branch stent is aligned with a coupling member disposed about the fenestration, the coupling member being expandable from a first configuration to a second configuration, and wherein a shape memory core is disposed in the coupling member;

b) radially expanding the branch stent via an expandable member disposed within the branch stent such that the engagement portion of the branch stent applies an expanding force to the coupling member, the expanding force operable to expand the coupling member from the first configuration to the second configuration; and c) removing the expanding force and allowing the coupling member to contract to a third configuration, the coupling member operable to apply a contracting force to the branch stent as the coupling member transitions from the second configuration to the third configuration.

\* \* \* \* \*